United States Patent
Arlot et al.

(10) Patent No.: US 8,106,089 B2
(45) Date of Patent: Jan. 31, 2012

(54) ANTI-TUBULIN ACTING ARYLPYRROL, ARYLFURAN AND ARYLTHIOPHENE DERIVATIVES, METHOD FOR THE PREPARATION THEREOF AND FOR THE USE THEREOF AS AN ANTIMITOTIC

(75) Inventors: Yannick Arlot, Thorigne-Fouillard (FR); Bénédicte Martin, Rennes (FR); Jean-Guy Delcros, Rennes (FR); Gilles Alcaraz, Rennes (FR); Olivier Paulus, Bretigny S/Orge (FR)

(73) Assignees: Centre National de la Recherche, Rennes (FR); Universite de Rennes 1, Rennes (FR)

( * ) Notice: Subject to any disclaimer, the term of this patent is extended or adjusted under 35 U.S.C. 154(b) by 1048 days.

(21) Appl. No.: 11/596,224

(22) PCT Filed: May 13, 2005

(86) PCT No.: PCT/FR2005/001207
§ 371 (c)(1),
(2), (4) Date: Dec. 4, 2007

(87) PCT Pub. No.: WO2005/115979
PCT Pub. Date: Dec. 8, 2005

(65) Prior Publication Data
US 2008/0275103 A1    Nov. 6, 2008

(30) Foreign Application Priority Data
May 14, 2004  (FR) ................... 04 05278

(51) Int. Cl.
*A61K 31/341* (2006.01)
*A61L 31/40* (2006.01)
*C07D 207/327* (2006.01)
*C07D 307/42* (2006.01)
*C07D 403/12* (2006.01)

(52) U.S. Cl. ........ 514/423; 514/427; 514/461; 534/551; 548/531; 548/562

(58) Field of Classification Search .................. None
See application file for complete search history.

(56) References Cited

U.S. PATENT DOCUMENTS

| 5,189,055 | A | * | 2/1993 | Thal et al. ............. 514/422 |
| 6,258,841 | B1 |  | 7/2001 | Uckun et al. |
| 6,559,374 | B2 | * | 5/2003 | Lindsey et al. ........... 136/263 |

FOREIGN PATENT DOCUMENTS

| FR | 1 472 992 | 9/1965 |
| WO | WO 90/02733 | 3/1990 |
| WO | WO 2004/029040 | 4/2004 |

OTHER PUBLICATIONS

Globub et al., "Molecular Classification of Cancer: Class Discovery and Class Prediction by Gene Expression Monitoring", Science, 286, 531-537, Oct. 15, 1999.*

Alazard, J., et al., "Composés interagissant avec in tubuline. Partie II, synthése de lactames tricycliques à squelette phénylpyrrole, analogues structuraux du rhazinilame",*Bull. Soc. Chim Fr*, (1996), 133:251-266.

Alazard, S., et al., "Composés interagissant avec la tubuline. Partie I: synthèse de phénylpyrroles *ortho-orthé* substitutés en rotation libre ou empechée", *Bull. Soc. Chim Fr* (1993), 130:779-787.

Dupont, C., et al., "Synthesis of a Rhazinilam Analogue Acting as an Inhibitor of Tubulin Assembly" *Tetrahedron Letters*, 2000. pp. 5853-5856, Elsevier Science Ltd.

Paulus, O. et al., "A Facile Synthesis of *N*-Boc-Protected Pyrroles by Cyclodehydration of *y*- Amino-alpha Beta-enals and -eones" *Eur. J. Org. Chem.*, 2002, pp. 2565-2572, Wiley-VCH Verlag GmbH, Germany.

Roskamp, E., et al., "A Regioselective Synthesis of Pyrroles via the Coupling of AlphaBeta-Unsaturated Immines with Esters or N,N-Dimethylformamide Promoted by NbC13(DME)," *J. Org. Chem.*, 1989, pp. 4736-4737, vol. 54, No. 20, American Chemical Society, USA.

Kin-Fai, C., et al., "Diastereoselective Addition Reactions of Furyl Aldehydes Using Chiral Boronates as Auxiliary: Application to the Enantioselective Synthesis of 2,3-disubstituted Furyl Alcohols," *Organic Letters*, 2001, pp. 3991-3994, vol. 3(25).

Kin-Fai, C., et al., "Diastereoselective Aldol Reactions of Furaldehyde Using a Chiral Boronate as Auxiliary: Application to the Synthesis of Enantiomerically Pure and Highly Functionalized 2,3-disubstituted Furanyl Alcohols," *Eur. J. Org. Chem.*, 2003, pp. 82-91, vol. 1.

Li, Q., et al., "Discovery and Development of Antimitotic Agents that Inhibit Tubulin Polymerisation for the Treatment of Cancer," *Expert Opin. Ther. Patents*, 2002, pp. 1663-1702, vol. 12(11).

Akai, S., et al., "Lipase-Catalyzed Domino Kinetic Resolution/ Intramolecular Diels-Alder Reaction: One-Pot Synthesis of Optically Active 7-oxabicyclo[2.2.1]heptenes from Furfuryl Alcohols and Beta-Substituted Acrylic Acids," *Chem. Eur. J.*, 2002, pp. 4255-4264, vol. 8(18).

International Search Report for PCT/FR2005/001207 completed Sep. 26, 2005.

International preliminary Report on Patentability for PCT/FR2005/001207 completed Jun. 14, 2006.

* cited by examiner

*Primary Examiner* — Fiona T Powers

(74) *Attorney, Agent, or Firm* — Alston & Bird LLP

(57) ABSTRACT

The invention relates to a compound represented by general formula (I) wherein Z represents N, O or S, and A represents a CH group, a nitrogen atom or an $NL^+$ group wherein L represents a straight-chained or branched $C_1$-$C_{12}$ alkyl group. The invention also relates to a method for the preparation thereof and the use thereof as an antimitotic.

12 Claims, No Drawings

ANTI-TUBULIN ACTING ARYLPYRROL, ARYLFURAN AND ARYLTHIOPHENE DERIVATIVES, METHOD FOR THE PREPARATION THEREOF AND FOR THE USE THEREOF AS AN ANTIMITOTIC

The present invention relates to novel arylpyrrol arylfuran and arylthiophene derivatives having an anti-tubulin action, advantageously an antimitotic action.

Within cell compartments there are a series of fibers which contribute to the shape and the texture of the cell. They constitute the cytoskeleton, which is primarily composed of actin microfilaments, microtubules and intermediate filaments, all of which are associated with protein complexes.

The network of microtubules plays an essential role in morphology, endocytosis, exocytosis and the cell cycle. The dynamics of microtubules in relation to guanosine triphosphate (GTP) is essential for the formation of the mitotic spindle. Consequently, microtubules are key elements in the segregation of chromosomes during meiosis and mitosis and thus they take part in the maintenance of genetic stability.

From an organizational point of view, microtubules are cylindrical structures which result from the longitudinal, helical assembly of 13 protofilaments which are formed by the association of tubulin molecules from one or more nucleation centers (microtubule organizing center, or MTOC) present in the cell. These organizing centers are the centrioles located in the cytoplasm. The majority of microtubules are the location of a rapid cycle of polymerization and depolymerization according to a dynamic instability model. The tubulin constituting the microtubules is a heterodimer globular protein made up of two polypeptide chains, α-tubulin and β-tubulin. These α and β heterodimers align in αβ alternation to form protofilaments. Heterodimers are polarized and consequently protofilaments and microtubules have an intrinsic polarity. Certain networks of microtubules have very different properties with regard to their stability, their geometry as well as their resistance with respect to certain antimitotic drugs. Cell division spindles are also labile structures that can be assembled and disassembled rapidly. A broad heterogeneity of microfilaments is concentrated in the C-terminal domain of the various tubulin isoforms, a domain which is involved in the association of MAPs (microtubule associated proteins).

MAPs act as a mediator between cell components and microtubules. They influence the dynamic structure of microtubules and co-purify with tubulin. Two types of MAPs are distinguished: structural MAPs (MAP2, tau protein, stable-tubule-only-polypeptide (STOP)) and motor MAPs with enzymatic activity (the kinesins and dynein). Double functionality can be provided by the same family of MAPs.

During cellular division, the microtubules forming the mitotic spindle function to segregate the duplicated chromosomes in order to orient them along the cleavage plane. The dynamics of the mitotic spindle thus allows the attachment of centromeres on the spindle microtubules and, after separation of the sister chromatids, the migration of the chromosomes to each pole of the mitotic spindle. This step is one of the events responsible for the transmission of genetic information from the mother cell to the daughter cell. Chromosomal abnormalities are one of the principal characteristics of cancer cells, thus highlighting the importance of maintaining perfectly stable genetic information. Some of these spindle formation or destruction abnormalities may have a role in cell transformation by the loss of a negative growth regulator gene, the loss of a gene responsible for the integrity of the genome, or by the amplification, the overexpression or the activation of an oncogene by mutation.

A tumor develops within an organ when some of its cells lose their contact inhibition property and divide indefinitely. One of the strategies used in the treatment of cancer consists of blocking cell division by targeting the machinery necessary for segregating chromosomes during mitosis.

Because of its functional diversity, tubulin and microtubules are the targets of choice for the treatment of cancer or of other diseases related to structural or organizational changes in this molecule such as autoimmune, hyperproliferative and neurodegenerative diseases. In addition, antimitotic agents acting on tubulin (tubulin binding agents) or on its associated proteins induce vascular damage and inhibit mitosis in tumors.

Molecules such as Taxol, vinblastine and colchicine are antimitotic compounds used in cancer therapy. Colchicine decreases the polymerization of microtubules. Taxol stabilizes microtubules by interacting on two specific sites on β-tubulin. It is a preferred antimitotic compound due to its microtubule stabilizing action.

The inventors have discovered in a surprising way that novel compounds called paulusines belonging to the family of arylpyrrol, arylfuran and arylthiophene compounds are capable of acting on the formation of the mitotic spindle and of controlling its functional integrity. Paulusines are original compounds synthesized to respond to the problems of genetic instability related to spindle formation abnormalities.

The present invention thus relates to compounds of following general formula I:

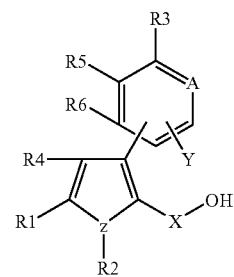

in which:

Z represents N, O or S,

R1, R3, R4, R5 and R6 represent independently of one another an atom of hydrogen, an atom of fluorine, a $C_1$-$C_{12}$ linear or branched alkyl group, a $C_3$-$C_{12}$ cycloalkyl group, a $C_2$-$C_{12}$ linear or branched alkenyl group, a $CH_2$—B or $CH_2$—$CH_2$—B group in which B represents a phenyl group possibly substituted by one or more groups chosen among a $C_1$-$C_6$ linear or branched alkyl group, a $C_1$-$C_6$ linear or branched alkoxy group, a $NH_2$ group, a $NO_2$ group, a CN group, a COOH group, a $C_1$-$C_6$ linear or branched $CO_2$(alkyl) group, a $CONH_2$ group, a $C_1$-$C_6$ linear or branched CONH(alkyl) group, a $C_1$-$C_6$ linear or branched CON(alkyl)$_2$ group, a Cl atom, a Br atom, an I atom, an OH group, a $COCF_3$ group, an $OSO_2CF_3$ group; a naphthyl group; an anthracenyl group; a 9H-fluorenyl group possibly substituted at position 9 by one or two $C_1$-$C_{12}$ linear or branched alkyl groups; an anisyl group or a pyridinyl group, R2 represents H, a $C_1$-$C_{12}$ linear or branched alkyl group, a phenyl group, a benzyl group, a $C_1$-$C_6$ linear or branched $CO_2$(alkyl) group, a $CO_2$(benzyl) group, a $C_2$-$C_6$ linear or branched $CO_2$(alkenyl) group, a tosyl group, a mesyl group, a 9-fluorenylmethoxycarbonyl (Fmoc) group, a $NH_2$ group or a $C_1$-$C_6$ linear or branched NH(alkyl) group, a $C_1$-$C_6$ linear or branched N(alkyl)$_2$ group, NH tertiobutyloxycarbonyl, $NHCO_2CH_2$ phenyl or R2 is absent when Z represents O.

x represents a $C_1$-$C_{12}$ linear or branched alkyl group, a $C_1$-$C_{12}$ linear or branched hydroxyalkyl group or a $C_1$-$C_{12}$ linear or branched aminoalkyl group.

A represents a CH group, a nitrogen atom or a $NL^+$ group in which L represents a $C_1$-$C_{12}$ linear or branched alkyl group.

Y represents an atom of hydrogen, a $C_1$-$C_{12}$ linear or branched alkyl group, a $C_3$-$C_{12}$ cycloalkyl group, an OH group, a CN group, a $N_3$ group, a $C_1$-$C_{12}$ linear or branched alkoxy group, a $C_1$-$C_{12}$ linear or branched hydroxyalkyl group, a $C_1$-$C_{12}$ linear or branched aminoalkyl group, $N_2^+$, a NZ1-NHZ2, NH—NZ1Z2 or NZ1Z2 group in which Z1 and Z2 represent independently of one another an atom of hydrogen, a $C_1$-$C_{12}$ linear or branched alkyl group, a $C_3$-$C_{12}$ cycloalkyl group, a phenyl group possibly substituted by one or more groups chosen among a $C_1$-$C_6$ linear or branched alkyl group, a $C_1$-$C_6$ linear or branched alkoxy group, a $NH_2$ group, a CN group, a COOH group, a $C_1$-$C_6$ linear or branched $CO_2$(alkyl) group, a $CONH_2$ group, a $C_1$-$C_6$ linear or branched CONH(alkyl) group, a $C_1$-$C_6$ linear or branched CON(alkyl)$_2$ group, a Cl atom, a Br atom, an I atom, an OH group, a $COCF_3$ group, an $OSO_2CF_3$ group, a benzyl group, an anisyl group, a pyridinyl group, C(O)—W, C(S)—W or C(NH)—W in which W represents a $C_1$-$C_{12}$ linear or branched alkyl group, a $C_3$-$C_{12}$ cycloalkyl group, a $C_1$-$C_{12}$ linear or branched alkoxy group, a $C_1$-$C_{12}$ linear or branched alkylthio group or NQQ1 in which Q and Q1 represent independently of one another an atom of hydrogen, a $C_1$-$C_{12}$ linear or branched alkyl group, a $C_3$-$C_{12}$ cycloalkyl group or $CH(M)CO_2M1$ in which M and M1 represent independently of one another a hydrogen atom, a $C_1$-$C_{12}$ linear or branched alkyl group, a $C_3$-$C_{12}$ cycloalkyl group, a $C_2$-$C_{12}$ linear or branched alkenyl group, a phenyl group, a benzyl group, a $CH_2$—B or $CH_2$—$CH_2$—B group in which B is as defined above.

In one embodiment of the present invention, the compound according to the present invention is such that Z represents N.

Advantageously, A represents the CH group.

In an advantageous way, Y represents a $NH_2$ group or an atom of hydrogen.

Advantageously, X represents a $C_1$-$C_{12}$ linear or branched alkyl group, advantageously a propyl group.

In a specific embodiment of the invention the compounds according to the present invention are selected from the group constituted of:

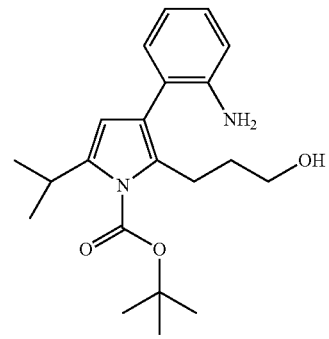

17

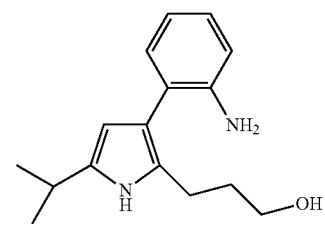

19

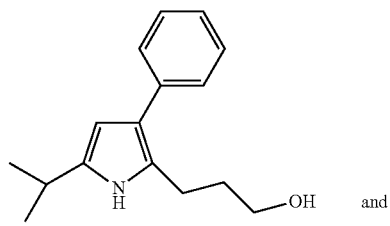

18 and

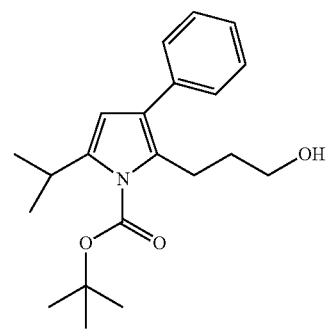

15

The present invention also relates to a method for preparing the compounds comprising the steps of:

a) synthesis of a pyrrolylalkylcarbinole, furanylalkylcarbinole or thiophenylalkylcarbinole unit of following general formula II:

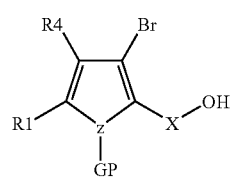

II in which Z, X, R1 and R4 are as defined above in general formula I and GP represents a nitrogen protective group when Z represents N, or is absent when Z represents O or S, b) functionalization of the pyrrolylalkylcarbinole, furanylalkylcarbinole, or thiophenylalkylcarbinole unit by introducing an aryl or heteroaryl unit at position 3 of the pyrrole, furan or thiophene ring.

Advantageously, in the case where X represents $(CH_2)_3$, step a) consists of the cyclodehydration of unsaturated β-γ aminoketones of following formula III:

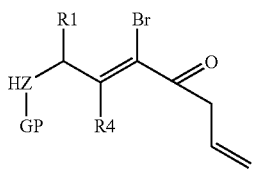

III in which Z, R1, R4 and GP are as defined above in general formula II in order to obtain the product of following formula IV:

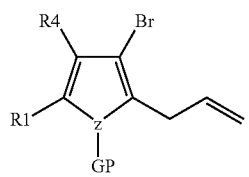

IV in which Z, R1, R4 and GP are as defined above in general formula II, followed by the introduction of the alcohol function by hydroboration-oxidation of the product of formula IV in order to obtain the product of formula II.

In an advantageous way, in the case where R2, R3, R4, R5 and R6 represent an atom of hydrogen, Y represents a $NH_2$ group, A represents a CH group, X represents $(CH_2)_3$ and Z represents N, step b) consists of:

a palladium-catalyzed Suzuki-Miyaura cross-coupling of the compound of formula II, in which R4 represents an atom of hydrogen, X represents $(CH_2)_3$, Z represents N and GP represents a nitrogen protective group, and of 2-triazene boronic acid in order to obtain a compound of following formula V:

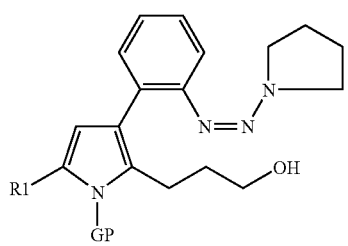

V in which GP represents a nitrogen protective group and R1 is as defined above in general formula I, deprotection of the triazene function in order to obtain the group of following formula VI:

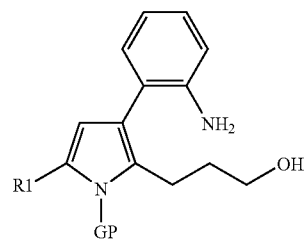

VI in which GP represents a nitrogen protective group and R1 is as defined above in general formula I, specific deprotection of protective group GP in order to obtain the compound of formula I in which R2, R3, R4, R5 and R6 represent an atom of hydrogen, Y represents a $NH_2$ group, A represents a CH group, X represents $(CH_2)_3$, Z represents N and R1 is as defined above in general formula I.

The synthesis methodology used is known to those skilled in the art and was adapted from a process described by Paulus et al. (*Eur. J. Org. Chem.* 2002, 2565-2572).

The synthesis of pyrrole-unit paulusines will be more specifically described.

Of course, many synthetic variations are possible for the development of a great number of related heterocyclic compounds.

The synthesis route is thus comprised of two stages.

The first stage consists of the synthesis of a functionalizable pyrrolylalkylcarbinole unit in the form of a N-protected 3-bromopyrrole with an alcohol side chain carried by the carbon in the a position of the ring's nitrogen.

The pyrrolylalkylcarbinole unit with the following general formula VII:

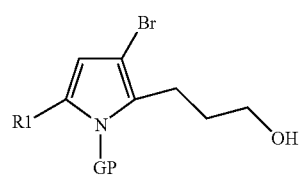

VII in which:

GP represents a nitrogen atom protective group, and

R1 is as defined in general formula I.

The polyfunctionalized pyrrole nucleus is obtained by cyclodehydration of unsaturated β-γ aminoketones (step v) with yields of 60% to 90%. These unsaturated β-γ aminoketones are most often obtained in several steps (i-iv, i) from commercial N-protected β-amino alcohols. In this manner, a N-protected 3-bromopyrrole with an unsaturated side chain is first obtained.

The alcohol function is then introduced in this case via a standard hydroboration-oxidation sequence (step vi) in a basic medium.

Method i-vi

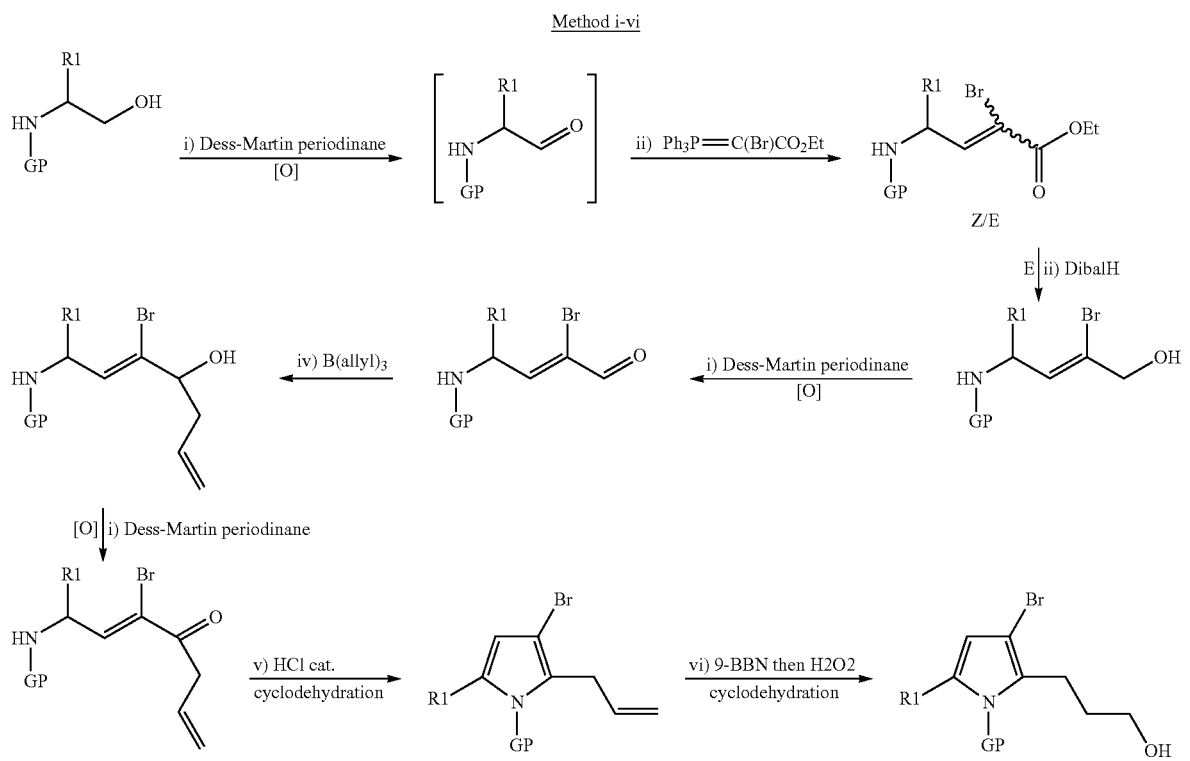

the second stage consists of functionalizing the pyrrolylalkylcarbinole unit by introducing the aryl or heteroaryl unit at position 3 of the pyrrole ring. In the example below, an aniline unit is introduced by a palladium-catalyzed Suzuki-Miyaura cross-coupling reaction. The aniline is introduced in an original protected form, that of a phenyltriazene, starting from 2-triazene boronic acid (step vii) which is also an original chemical. A triazene function deprotection step makes it possible in the end to regenerate the amino function of the aniline nucleus (step viii). Then, a specific deprotection step for the protective group (GP) used can then be implemented if necessary to obtain the corresponding N-deprotected anilinopyrrolyl alcohol.

Method vii - viii

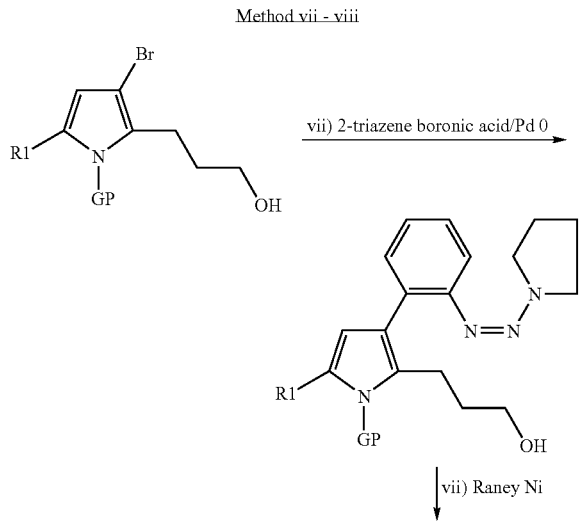

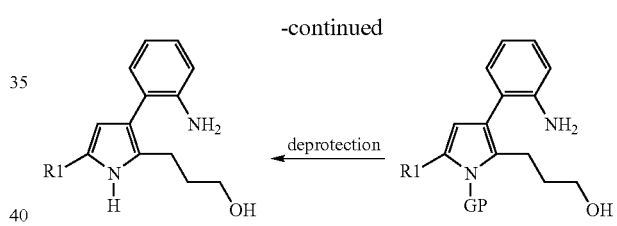

Of course, this synthesis route is not restricted to the introduction of an anilino unit only.

The present invention also relates to a pharmaceutical composition comprising a compound according to the present invention and a pharmaceutically acceptable excipient, a compound for the use thereof as a medicine, advantageously antimitotic, in an advantageous way antitumoral.

This medicine can also be intended for the treatment of autoimmune diseases, hyperproliferative diseases and neurodegenerative diseases.

The present invention also relates to a compound according to the present invention for the use thereof as a medicine intended for the treatment or prevention of cancer.

The present invention thus relates to pharmaceutical compositions comprising one of the compounds defined above as an active ingredient and a suitable excipient. These compositions can be formulated for administration to mammals, including man. Dosage varies according to the treatment and to the affection in question. These compositions are prepared in such a way that they can be administered by the digestive or the parenteral route.

In the pharmaceutical compositions of the present invention for oral, sublingual, subcutaneous, intramuscular, intravenous, transdermal, local or rectal administration, the active ingredient can be administered in single-dose forms, in a mixture with traditional pharmaceutical vehicles, to animals or to humans. Suitable single-dose forms of administration include oral-route forms such as tablets, gelatin capsules, powders and granules, oral solutions or suspensions, sublingual and buccal administration forms, as well as subcutaneous, intramuscular, intravenous, intranasal, intraocular and rectal forms of administration.

When a solid composition in tablet form is prepared, the principal active ingredient is mixed with a pharmaceutical vehicle such as gelatin, starch, lactose, magnesium stearate, talc, gum arabic or analogs. The tablets can be coated with sucrose or with other suitable substances or they can be treated in such a way that they have an extended or delayed activity and that they continuously release a predetermined quantity of the active ingredient.

A gelatin capsule preparation is obtained by mixing the active ingredient with a diluent and by pouring the mixture obtained into soft or hard gelatin capsules.

A preparation in syrup or elixir form can contain the active ingredient in conjunction with a sweetener, an antiseptic, as well as an agent providing flavor and a suitable colorant.

Water-dispersible powders or granules can contain the active ingredient in a mixture with dispersion, wetting or suspending agents, as well as with taste correctors or sweeteners.

Suppositories prepared with excipients that melt at rectal temperature, such as cocoa butter or polyethylene glycols, can be used for rectal administration.

For parenteral, intranasal or intraocular administration, aqueous suspensions, isotonic saline solutions or sterile injectable solutions which contain pharmacologically compatible dispersion and/or wetting agents are used.

The active ingredient can also be formulated in the form of microcapsules, possibly with one or more additional vehicles.

The present invention further relates to compounds of following general formula V:

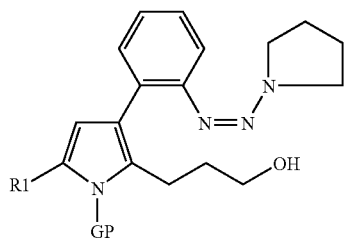

V in which GP represents a nitrogen protective group and R1 represents an atom of hydrogen, an atom of fluorine, a $C_1$-$C_{12}$ linear or branched alkyl group, a $C_3$-$C_{12}$ cycloalkyl group, a $C_2$-$C_{12}$ linear or branched alkenyl group, a $CH_2$—B or $CH_2$—$CH_2$—B group in which B represents a phenyl group possibly substituted by one or more groups chosen among a $C_1$-$C_6$ linear or branched alkyl group, a $C_1$-$C_6$ linear or branched alkoxy group, a $NH_2$ group, a $NO_2$ group, a CN group, a COOH group, a $C_1$-$C_6$ linear or branched $CO_2$(alkyl) group, a $CONH_2$ group, a $C_1$-$C_6$ linear or branched CONH(alkyl) group, a $C_1$-$C_6$ linear or branched CON(alkyl)$_2$ group, a Cl atom, a Br atom, an I atom, an OH group, a $COCF_3$ group, an $OSO_2CF_3$ group, a naphthyl group; an anthracenyl group; a 9H-fluorenyl group possibly substituted at position 9 by one or two $C_1$-$C_{12}$ linear or branched alkyl groups; an anisyl group or a pyridinyl group.

The present invention further relates to a compound of following general formula VI:

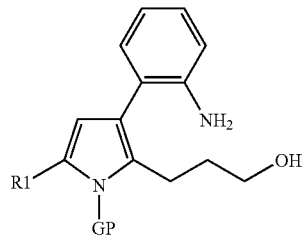

VI in which GP represents a nitrogen protective group and R1 represents an atom of hydrogen, an atom of fluorine, a $C_1$-$C_{12}$ linear or branched alkyl group, a $C_3$-$C_{12}$ cycloalkyl group, a $C_2$-$C_{12}$ linear or branched alkenyl group, a $CH_2$—B or $CH_2$—$CH_2$—B group in which B represents a phenyl group possibly substituted by one or more groups chosen among a $C_1$-$C_6$ linear or branched alkyl group, a $C_1$-$C_6$ linear or branched alkoxy group, a $NH_2$ group, a $NO_2$ group, a CN group, a COOH group, a $C_1$-$C_6$ linear or branched $CO_2$(alkyl) group, a $CONH_2$ group, a $C_1$-$C_6$ linear or branched CONH(alkyl) group, a $C_1$-$C_6$ linear or branched CON(alkyl)$_2$ group, a Cl atom, a Br atom, an I atom, an OH group, a $COCF_3$ group, an $OSO_2CF_3$ group; a naphthyl group; an anthracenyl group; a 9H-fluorenyl group possibly substituted at position 9 by one or two $C_1$-$C_{12}$ linear or branched alkyl groups; an anisyl group or a pyridinyl group.

The following examples are indicative and nonrestrictive.

I. EXAMPLE 1

Preparation of Compounds 17, 18, 19

The general synthesis route is as follows:

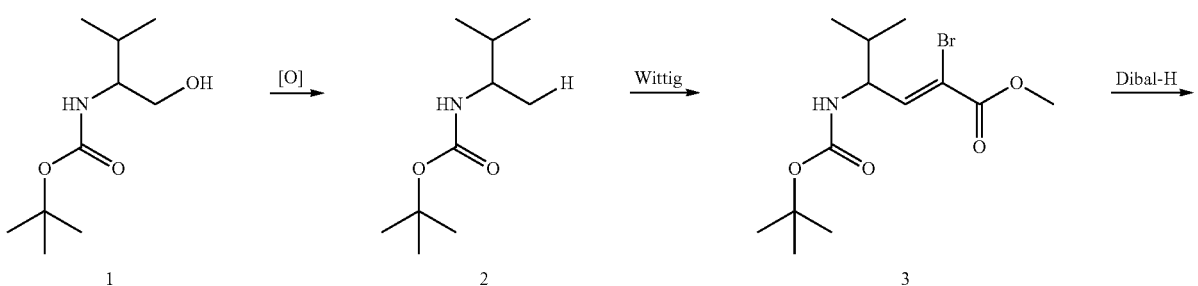

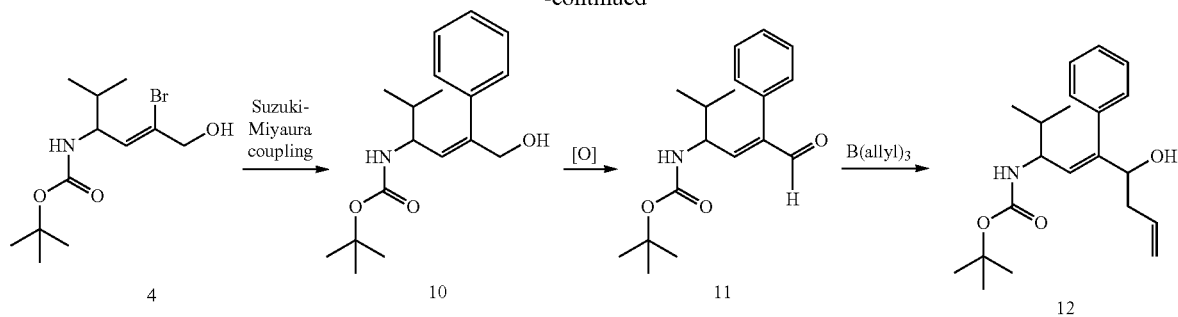
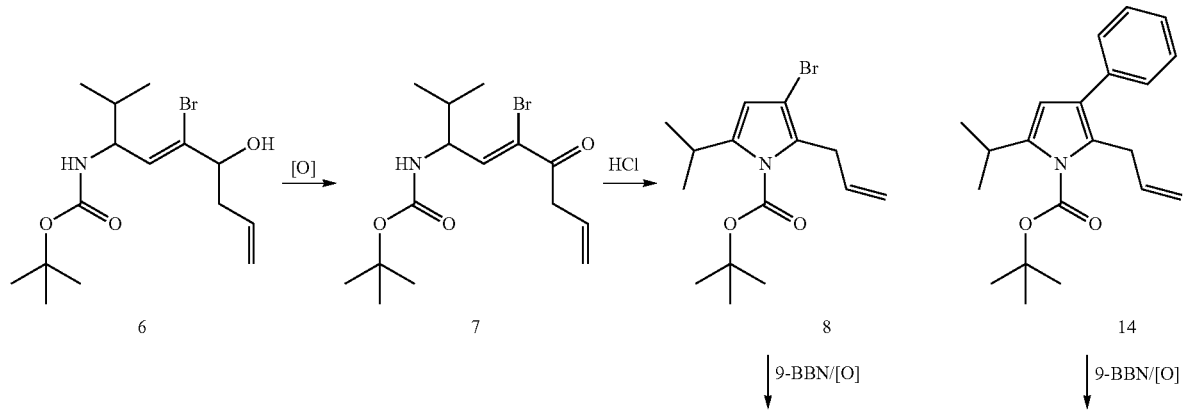
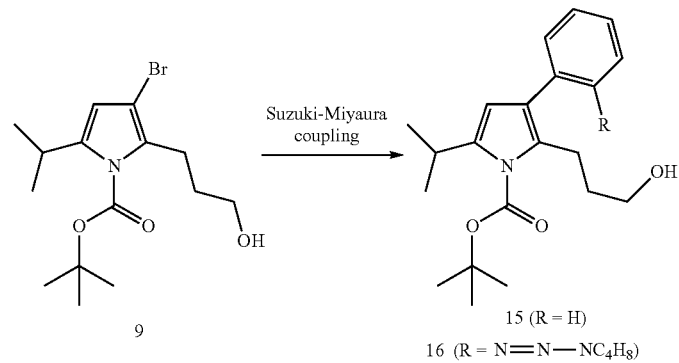

The Suzuki-Miyaura coupling that makes it possible to obtain compound 16 from compound 9 corresponds to the following reaction route:
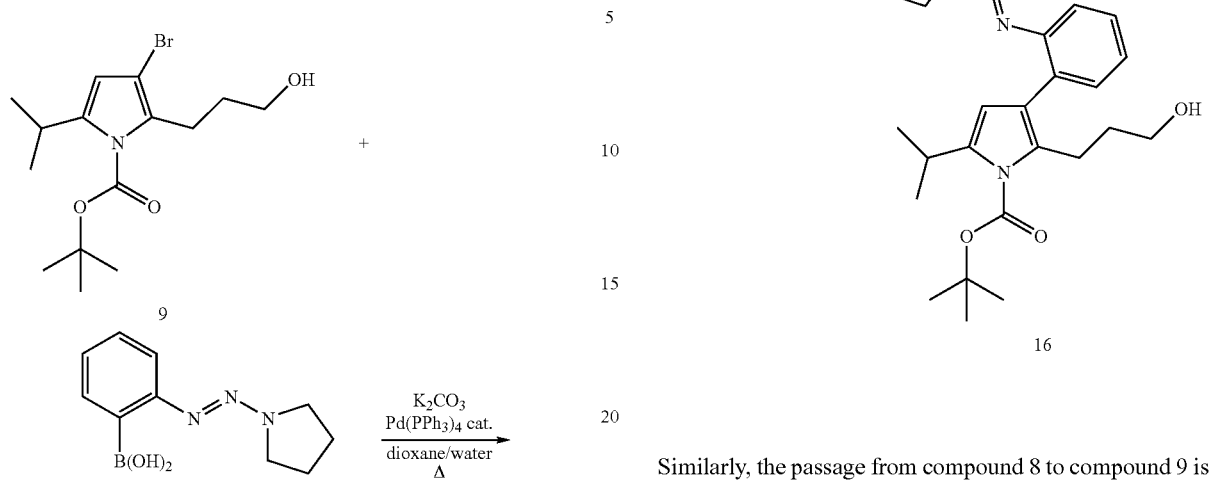
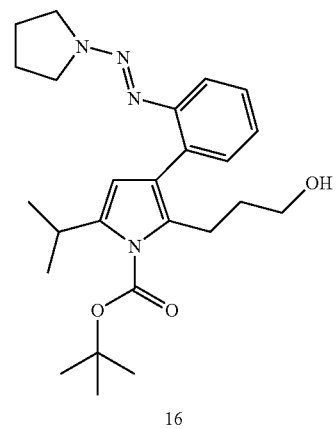
Similarly, the passage from compound 8 to compound 9 is accomplished according to the following reaction:
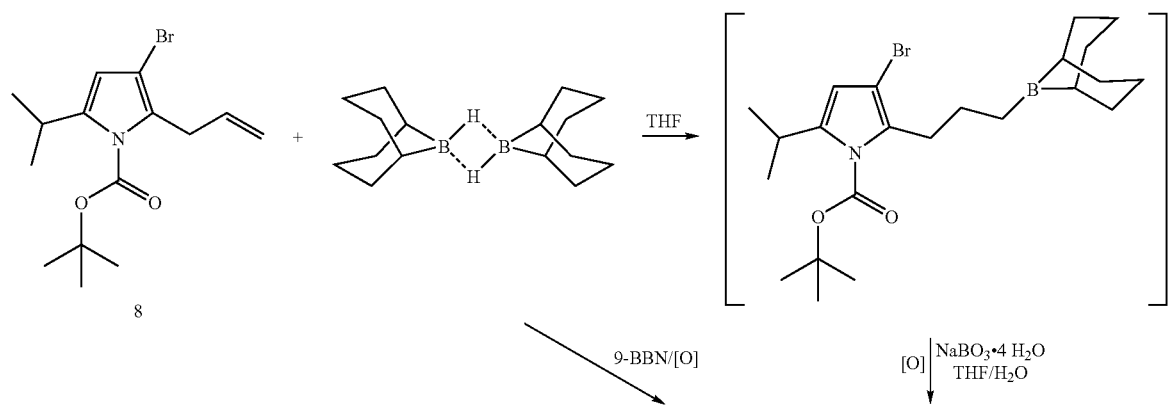
[9-BBN: 9-9-borabicyclo[3.3.1]nonane dimer
[O]: oxidation
NaBO3-4H2O: sodium perborate tetrahydrate]
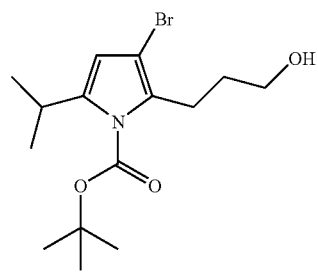

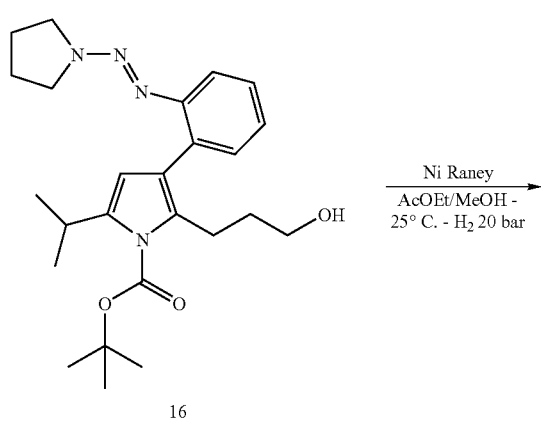

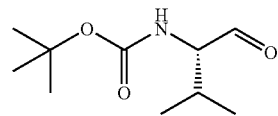

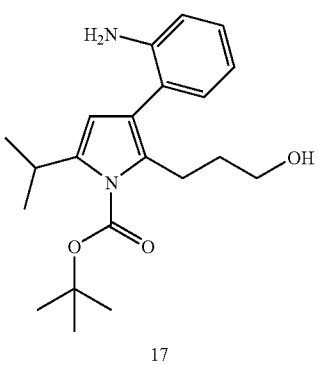

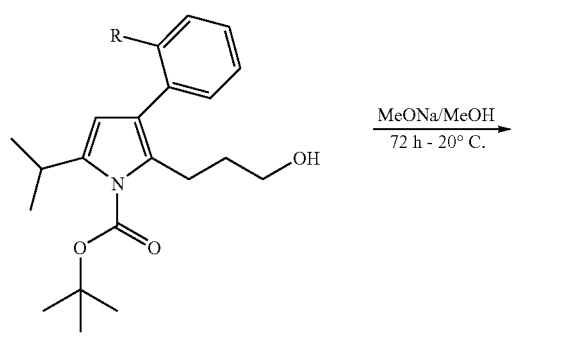

15 (R = H)
17 (R = NH₂)

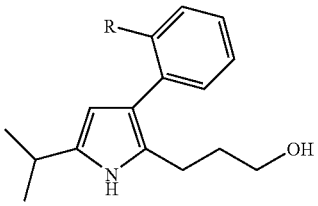

18 (R = H)
19 (R = NH₂)

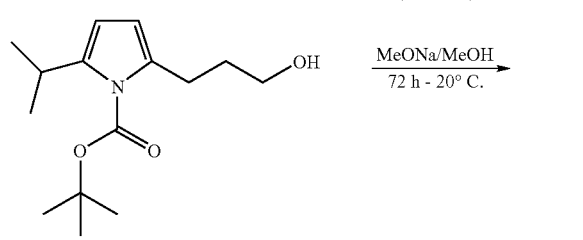

20

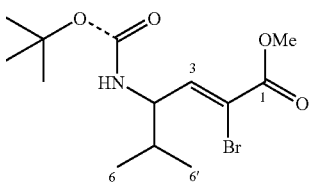

21

For compounds 1 and 2, the method used is that described in the Paulus et al. article (*Eur. J. Org. Chem.* 2002, 2565-2572).

(S)—N-(tert-Butoxycarbonyl)valinal (2)

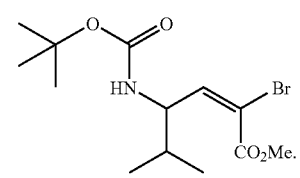

Pale yellow oil.
Rf=0.45 (AcOEt/Hept 1/1)
NMR (200 MHz, CDCl₃) ¹H: δ
0.87 and 0.96 d, 6H, ³J=7.0 Hz, CH₃)
1.38 (s, 9H, (CH₃)₃)
2.20 (m, 1H, CH(CH₃)₂)
4.15 (m, 1H, CH)
5.12 (d broad, 1H, NH)
9.55 (s, 1H, CHO)
NMR (50 MHz, CDCl₃) ¹³C: δ
17.9 and 19.4 (CH₃)
28.6 [(CH₃)₃]
29.4 [CH(CH₃)₂]
65.0 (CH)
80.2 [C(CH₃)₃]
156.2 (NCO)
200.8 (CHO)

Methyl(2Z)-2-bromo-4-[N-(tert-butoxycarbonyl)amino]-5-methylhexenoate (Z-3) and its isomer (E-3)

N-Bromosuccinimide (4.60 g, 25.9 mmol) and anhydrous potassium carbonate (8.10 g, 58.8 mmol) are successively added, over a period of 20 minutes, to a solution of (methoxycarbonylmethylene)triphenylphosphorane (PH₃P=CH—CO₂Me, 7.90 g, 23.5 mmol) in dichloromethane (60 ml) cooled to −20.0° C. The mixture, yellow-brown, is left under stirring for 20 min and freshly prepared N-(Boc)Valinal 2 (4.74 g, 23.5 mmol) dissolved in $CH_2Cl_2$ (20 ml) is instilled. The addition completed, the mixture is left for 30 min at −20.0° C. and for 1 h at ambient temperature. A TLC check indicates the total disappearance of the aldehyde. The mixture is filtered on a fritted disc coated with celite, and the fritted disc is rinsed with ether. After evaporation of the filtrate under a vacuum, the yellow oil obtained is chromatographed on a silica gel (elution gradient Heptane/AcOEt 90/10→75/25). 2.10 g (27%, Rf=0.46 (AcOEt/Hept 1/3)) of pure isomer E, 0.63 g of mixture (7%, Z+E) and 3.2 g (41%, Rf=0.35 (AcOEt/Hept 1/3)) of pure isomer Z are obtained.

Yield=75%

Compound Z-3 is a colorless oil.

$^1$H NMR (200 MHz, $CDCl_3$): δ1.00 (d, 6H, $^3$J=6.8 Hz, $H_6$ and $H_{6'}$), 1.48 (s, 9H, $(CH_3)_3$), 1.97 (m, 1H, Hs), 3.88 (s, 3H, OMe), 4.42 (s broad, 1H, $H_4$), 4.69 (s broad, 1H, NH), 7.17 (d, 1H, $^3$J=6.8 Hz, $H_3$)

$^{13}$C NMR (50 MHz, $CDCl_3$): δ17.2 and 17.8 (C6 and C6'), 27.3 [$(CH_3)_3$], 31.1 (C5), 52.4 ($OCH_3$), 56.2 (C4), 78.8 [$C(CH_3)_3$], 115.4 ($C_2$), 144.2 ($C_3$), 154.3 (NC=O), 161.8 (C1)

Compound E-3 is a colorless oil.

$^1$H NMR (200 MHz, $CDCl_3$): δ0.78 (d, $^3$J=6.8 Hz, $H_6$ and $H_{6'}$), 1.26 (s, 9H, $(CH_3)_3$), 1.72 (m, 1H, $H_5$), 3.67 (s, 3H, OMe), 4.53 (m, 2H, NH+$H_4$), 6.32 (d, 1H, $^3$J=7.0 Hz, $H_3$)

$^{13}$C NMR (50 MHz, $CDCl_3$): δ18.5 and 19.4 (C6 and C6'), 28.7 [$(CH_3)_3$], 32.9 (C5), 53.5 ($OCH_3$), 56.1 (C4), 80.0 [$C(CH_3)_3$], 113.0 (C2), 148.2 (C3), 156.7 (NC=O), 163.4 (C1)

Elemental analysis (E+Z mixture):

calculated: 46.44% C, 6.60% H, 4.17% N measured: 46.66% C, 6.81% H, 4.05% N (2Z)-2-bromo-4-[N-(tert-butoxycarbonyl)amino]-5-methylhex-2-en-1-ol (4) $C_{12}H_{22}BrNO_3$ M=308 g/mol

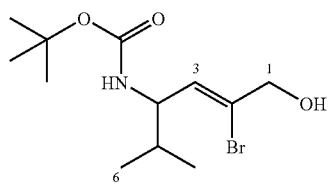

4

To a solution of ester Z-3 (2.60 g, 7.7 mmol) in dichloromethane (50 ml), cooled to −78° C., 990 μl (1.0 eq) of freshly distilled $BF_3.OEt$ is instilled over a period of 15 minutes and then 23.4 ml (3.0 eq) of DIBAL (1 M solution/toluene) is instilled over a period of one hour. The reaction mixture is maintained at −78° C. for 3 h then is neutralized at −50° C. by the slow addition of 5 ml of acetic acid. At 0° C., 30 ml of an aqueous solution saturated with $NH_4Cl$ are added. The gel formed is broken by the addition of an aqueous solution saturated with citric acid while taking care not to go below pH 3-4. The aqueous phase is extracted with AcOEt. The recombined organic phases are washed with brine and dried on $MgSO_4$. After filtration and evaporation of the solvent, the yellow oil obtained is purified on a silica gel (AcOEt/Hept 1/2), leading to a colorless oil which, after trituration with pentane and prolonged drying with a vane pump, crystallizes in the form of a white solid (1.73 g, 5.6 mmol).

Yield=72%

Rf=0.45 (AcOEt/Hept 1/1)

m.p.=74-76° C.

$^1$H NMR (200 MHz, $CDCl_3$): δ0.96 (d, 6H, $^3$J=6.8 Hz, $H_6$ and $H_{6'}$), 1.46 (s, 9H, $(CH_3)_3$), 1.90 (s broad, 1H, $H_5$), 2.00 (s broad, 1H, OH), 4.27 (d, 2H, $^3$J=1.2 Hz, $H_1$), 4.30 (m, 1H, $H_4$), 4.58 (s broad, 1H, NH), 5.98 (d, 1H, $^3$J=8.6 Hz, $H_3$)

$^{13}$C NMR (50 MHz, $CDCl_3$): δ18.6 and 19.1 (C6 and C6'), 28.8 [$(CH_3)_3$], 32.9 (C5), 57.3 (C4), 68.2 (C1), 79.9 [$C(CH_3)_3$], 128.5 (C2), 128.9 (C3), 156.5 (NC=O)

HRMS (EI): m/z calculated for $C_9H_{15}^{79}BrNO_3$ ([M-$C_3H_7$]$^{+}$): 264.0235; measured: 264.0242

Elemental analysis:

calculated: 46.76% C, 7.19% H, 4.54% N measured: 46.93% C, 7.35% H, 4.39% N (2Z)-2-bromo-4-[N-(tert-butoxycarbonyl)amino]-5-methylhex-2-enal (5)

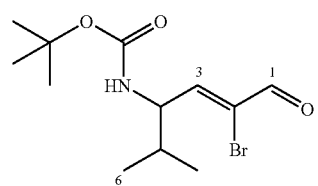

5

Dess-Martin periodinane (630 mg, 1.3 eq) is added all at once to a solution of allyl alcohol 4 (347 mg, 1.1 mmol) in $CH_2Cl_2$ (15 ml). The reaction mixture is stirred for 1 h at ambient temperature before dilution with ether and neutralization with an aqueous solution saturated with $Na_2S_2O_3$ (15 ml) and an aqueous solution saturated with $NaHCO_3$ (15 ml). The aqueous phase is extracted with ether then the recombined organic phases are washed with brine and dried on $MgSO_4$. After filtration and evaporation of the solvent, the residual oil obtained is purified by filtration on an alum tube coated with 2-3 cm of silica (eluant: $Et_2O$) leading to the enal 5 (324 mg, 1.06 mmol, clean in 1H NMR) in the form of a colorless oil.

Yield=95%

Rf=0.55 (AcOEt/Hept 1/1)

$^1$H NMR (300 MHz, $CDCl_3$): 0.96 and 0.98 (d, 6H, $^3$J=6.8 Hz, $H_6$ and $H_{6'}$), 1.37 (s, 9H, $(CH_3)_3$), 1.99 (s broad, 1H, $H_5$), 4.46 (m, 1H, $H_4$), 4.95 (s broad, 1H, NH), 6.99 (d, 1H, $^3$J=7.3 Hz, $H_3$), 9.17 (s, 1H, $H_1$)

$^{13}$C NMR (75 MHz, $CDCl_3$): δ

18.3 and 19.0 (C6 and C6'), 28.4 [$(CH_3)_3$], 32.1 (C5), 57.2 (C4), 80.2 [$C(CH_3)_3$], 128.5 (C2), 153.8 (C3), 155.3 (NC=O), 186.1 (CHO)

HRMS (EI):

m/z calculated for $C_8H_{12}^{79}BrNO_3$ ([M-$C_4H_8$]$^{+}$): 249.0000; measured: 248.9997 m/z calculated for $C_9H_{13}^{79}BrNO_3$ ([M-$C_3H_7$]$^{+}$): 262.0078; measured: 262.0078

Elemental analysis:

calculated: 47.07% C, 6.58% H, 4.57% N measured: 47.12% C, 6.65% H, 4.46% N

5-methyl-4(N-tert-Butoxycarbonyl)amino-2-bromo-1-allyl-(2Z)-hexen-1-ol (6)

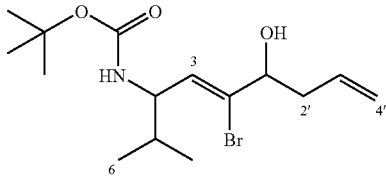

The triallylborane (460 µl, 2.42 mmol) is slowly added to a solution of enal 5 (370 mg, 1.21 mmol) in tetrahydrofuran (THF) (10 ml) cooled to −70° C. After 1 h of stirring, the mixture is allowed to rise in temperature and is neutralized at 0° C. with an aqueous solution saturated with $NH_4Cl$ (10 ml). After separation of the phases and extraction in AcOEt, the recombined organic phases are washed with brine, dried on $MgSO_4$ and filtered. The residual oil obtained after evaporation of the solvent is purified on a silica gel (AcOEt/Hept 1/2) leading to the alcohol 6 (385 mg, 1.11 mmol) which is obtained in the form of a colorless oil.

Yield=92%

Rf=0.51 (AcOEt/Hept 1/1)

Mix of two diastereoisomers D1 and D2 in a 50/50 proportion according to 1H NMR.

$^1$H NMR (300 MHz, $CDCl_3$): δ0.92 (m, 6H, $^3J$=6.8 Hz, $H_6$), 1.44 (S, 9H, $(CH_3)_3$), 1.85 (s broad, 1H, $H_5$), 2.38-2.53 (m, 3H, $H_2$+OH), 4.16 and 4.19 (t, 1H, $^3J$=6.1 Hz, $H_1$), 4.30 (s broad, 1H, $H_4$), 4.59 (s broad, 1H, NH), 5.11 (d, 1H, $^3J$=9.1 Hz, $H_{4'cis}$), 5.15 (d, 1H, $^3J$=15.3 Hz, $H_{4'trans}$), 5.72 (m, 1H, $H_{3'}$), 5.87 and 5.91 (d, 1H, $^3J$=8.7 Hz, $H_3$)

$^{13}$C NMR (75 MHz, CDCb): δ18.4 and 18.7 (C6 and C6'), 28.4 $[(CH_3)_3]$, 32.5 (C5), 40.0 (C2'), 56.8 (C4), 75.5 (C1), 79.8 $[C(CH_3)_3]$, 118.6 (C4'), 129.0 and 129.7 (C3'), 131.5 and 131.9 (C2), 133.2 and 133.3, (C3), 155.3 (NC=O)

HRMS (EI): m/z calculated for $C_{12}H_{19}NO_3^{79}Br$ ([M-$C_3H_7$']$^+$): 304.0548; measured: 304.0541

Elemental analysis:

calculated: 51.73% C, 7.52% H, 4.02% N measured: 51.92% C, 7.63% H, 4.05% N

(2z)-5-Methyl-4(N-tert-butoxycarbonyl)amino-2-bromo-1-allylhexen-1-one (7)

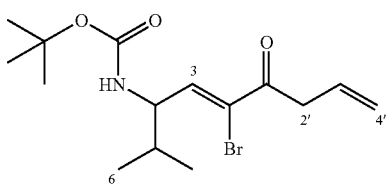

Dess-Martin periodinane (640 mg, 1.51 mmol) is added to a solution of alcohol 6 (350 mg, 1.00 mmol) in dichloromethane (10 ml) and it mixture is left until the alcohol completely disappears as shown by TLC (1 h). The mixture is then diluted with ether and evaporated under a vacuum. The crude product is taken up in a mixture of AcOEt/Hept (3 ml, 1/3 v/v) then filtered on a silica gel (4-5 cm in an alum tube, eluent AcOEt/Hept 1/3) leading after collection of the fractions and evaporation of the solvent to the enone 7 (325 mg, 0.94 mmol) in the form of a colorless oil.

Yield=94%

Rf=0.64 (AcOEt/Hept 1/1)

$^1$H NMR (200 MHz, $CDCl_3$): δ1.01 (d, 6H, $^3J$=6.8 Hz, $H_6$), 1.47 (s, 9H, $(CH_3)_3$), 1.99 (s broad, 1H, $H_5$), 3.62 (dm, 2H, $^3J$=6.6 Hz, $H_{2'}$), 4.44 (s broad, 1H, $H_4$), 4.78 (s broad, 1H, NH), 5.19 (dm, 1H, $^3J$=16.9 Hz, $H_{4'trans}$), 5.27 (dm, 1H, $^3J$=10.3 Hz, $H_{4'cis}$), 5.98 (ddt, 1H, $^3J$=17.1 Hz, $^3J$=10.4 Hz, $^3J$=6.6 Hz, $H_{3'}$), 7.02 (d, 1H, $^3J$=8.3 Hz, $H_3$)

$^{13}$C NMR (50 MHz, $CDCl_3$): δ18.6 (C6), 119.6 (C4'); 19.3 (C6'), 126.4 (C2), 28.8 $[(CH_3)_3]$, 130.8 (C3') 32.5 (C5), 144.2 (C3), 44.1 (C2'); 155.7 (NC=O), 58.1 (C4), 192.7 (CHO), 80.4 $[C(CH_3)_3]$

HRMS (EI): m/z calculated for $C_{12}H_{17}NO_3^{79}Br$ ([M-$C_3H_7$']$^+$): 302.0392; measured: 302.0380

1-(tert-Butoxycarbonyl)-2-isopropyl-4-bromo-5-allylpyrrole (8)

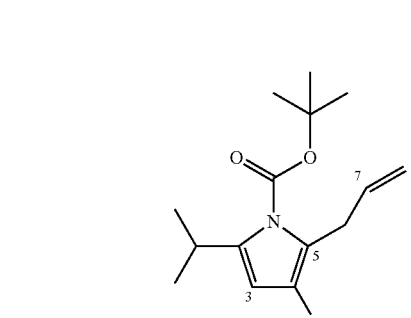

A solution of enone 7 (310 mg, 0.90 mmol) in dichloromethane (10 ml) is acidified by HCl (450 µl, 2 M solution in $Et_2O$) and the mixture is stirred at ambient temperature. The progress of the reaction is followed by TLC and after the disappearance of the starting product the reaction mixture is neutralized with an aqueous solution saturated with $NaHCO_3$ (10 ml). After separation of the phases and extraction of the aqueous phase in AcOEt, the organic phases are recombined, washed with brine, dried on $MgSO_4$ and then filtered. The oil obtained after evaporation of the solvent is purified on a silica gel (AcOEt/Hept 1/6) leading to the pyrrole 8 (195 mg, 0.59 mmol) in the form of a colorless oil.

Yield=66%

Rf=0.73 (AcOEt/Hept 1/3)

$^1$H NMR (300 MHz, $CDCl_3$): δ1.19 (d, 6H, $^3J$=6.8 Hz, $CH_3$), 1.59 (s, 9H, $(CH_3)_3$), 3.42 (app quint, 1H, $^3J$=6.8 Hz, $CH(CH_3)_2$), 3.61 (dm, 2H, $^3J$=5.6 Hz, $H_6$), 4.92 (dm, 1H, $^3J$=17.3 Hz, $H_{8trans}$), 5.03 (dm, 1H, $^3J$=10.3 Hz, $H_{8cis}$), 5.89 (ddt, 1H, $^3J$=17.3, 10.3 and 5.6 Hz, $H_7$), 5.98 (d, 1H, $^4J$=0.9 Hz, $H_3$)

$^{13}$C NMR (75 MHz, $CDCl_3$): δ23.1 $(CH_3)$, 27.1 [CH $(CH_3)_2$], 28.1 $[(CH_3)_3]$, 31.2 (C6), 84.5 $[C(CH_3)_3]$, 101.1 (C4), 109.7 (C3), 115.4 (C8), 129.2 (C5), 135.4 (C7), 142.8 (C2), 149.5 (NC=O)

HRMS (EI): m/z calculated for $C_{15}H_{22}N^{79}BrO_2$ ([M]$^+$): 327.0834; measured: 327.0837

N-(tert-Butoxycarbonyl)-2-isopropyl-4-bromo-5-(3-hydroxypropyl)pyrrole (9)

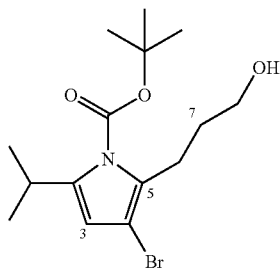

Under an argon atmosphere, a solution of 9-BBN (216 mg, 1.77 mmol) in THF (3 ml), cooled to −20° C., is slowly added to a solution of pyrrole 8 (195 mg, 0.59 mmol) in THF (2 ml). The mixture is left for 30 minutes at −20° C. followed by 20 h under stirring at ambient temperature. 1 ml of EtOH (16.9 mmol), 420 µl of 5 N soda (2.1 mmol) and 720 µl of 35% hydrogen peroxide (in weight in water/1 ml=9.33 mmol/6.71 mmol) are then added in succession. The mixture is immediately brought to reflux. After 30 minutes, 10 ml of brine are added. The mixture is extracted in AcOEt. The organic phases are dried on MgSO$_4$ then concentrated under a vacuum. The yellow oil obtained is purified on a silica gel (AcOEt/Hept 1/3) leading to the alcohol 9 (98 mg, 0.28 mmol) in the form of a colorless oil.

Yield=48%
Rf=0.21 (AcOEt/Hept 1/3)
$^1$H NMR (200 MHz, CDCl$_3$): δ1.21 (d, 6H, $^3$J=6.8 Hz, CH$_3$), 1.64 (s, 9H, (CH$_3$)$_3$), 1.84 (quint, 3H, $^3$J=7.3 Hz, H$_7$+OH), 2.96 (t, 2H, $^3$J=7.1 Hz, H$_6$), 3.41 (app quint, 1H, $^3$J=6.8 Hz, CH(CH$_3$)$_2$), 3.66 (t, 2H, $^3$J=6.3 Hz, H$_8$), 5.98 (d, 1H, $^4$J=1.0 Hz, H$_3$)
$^{13}$C NMR (50 MHz, CDCl$_3$): δ23.4 (CH$_3$), 85.1 [C(CH$_3$)$_3$], 23.7 (C6), 101.0 (C4), 27.6 [CH(CH$_3$)$_2$], 110.1 (C3), 28.3 [(CH$_3$)$_3$], 132.0 (C5), 32.8 (C7), 142.8 (C2), 62.3 (C8), 150.1 (NC=O)
HRMS (EI): m/z calculated for $C_{15}H_{24}^{79}BrNO_3$ ([M]$^+$): 345.0939; measured: 345.0923

(2E),5-methyl-4-(N-tert-butoxycarbonyl)amino-2-phenyl-2-hexen-1-ol (10)

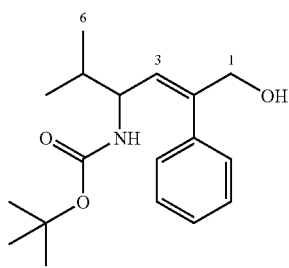

A dioxane/H$_2$O mixture (degassed) (10 ml, 4/1 v/v) containing the bromated alcohol 4 (770 mg, 2.5 mmol), phenyl-boronic acid (335 mg, 1.1 eq), potassium carbonate (690 mg, 2.0 eq) and Pd(Ph$_3$)$_4$ (90 mg, 0.03 eq) is brought to reflux for 8 h under argon. Upon return to ambient temperature the mixture is filtered on an alum tube filled with a bed of several centimeters of celite. An aqueous solution saturated with NaCl (10 ml) is added to the filtrate. After separation of the phases and extraction of the aqueous phase in AcOEt, the organic phases are washed with brine and dried on MgSO$_4$ before being concentrated under a vacuum. The oil obtained is purified on a silica gel (AcOEt/Hept 1/2) leading to alcohol 10 (690 mg, 2.3 mmol) in the form of a pale yellow foam.

Yield=90%
Rf=0.38 (AcOEt/Hept 1/1)
$^1$H NMR (200 MHz, CDCl$_3$): δ0.83 (d, 6H, $^3$J=6.8 Hz, H$_6$), 1.44 (s broad, 9H, (CH$_3$)$_3$), 1.70 (m, 1H, H$_5$), 2.23 (m, 1H, OH), 4.00 (m, 1H, H$_4$), 4.27 (dd, 2H, $^3$J=7.7 Hz, $^4$J=1.2 Hz, H$_1$), 4.55 (d broad, 1H, $^3$J=7.7 Hz, NH), 6.62 (dt, 1H, $^3$J=9.7 Hz, $^4$J=1.4 Hz, H$_3$), 7.25-7.43 (m, 5H, Har)
Note: 2 rotamers are detected at ambient temperature by 13C.
$^{13}$C NMR (75 MHz, CDCl$_3$): δ18.3 (C6), 18.5 (C6'), 28.3 [(CH$_3$)$_3$], 33.2, 33.4 (C5), 54.0, 55.0 (C4), 66.9 (C1), 78.8, 79.3 [C(CH$_3$)$_3$], 125.3 (C3), 127.2 (CHar), 128.2 (CHar), 128.4 (CHar), 138.0 ($^{IV}$Car), 142.7 (C2), 155.1, 155.9 (NC=O)
HRMS (EI):
m/z calculated for $C_{15}H_{20}NO_3$ ([M-C$_3$H$_7$']$^+$): 262.1443; measured: 262.1457
m/z calculated for $C_{14}H_{19}NO_3$ ([M-C$_4$H$_8$]$^+$): 249.1365; measured: 249.1383

5-Methyl-4-(N-tert-butoxycarbonyl)amino-2-phenyl-(2E)-hexen-1-al (11)

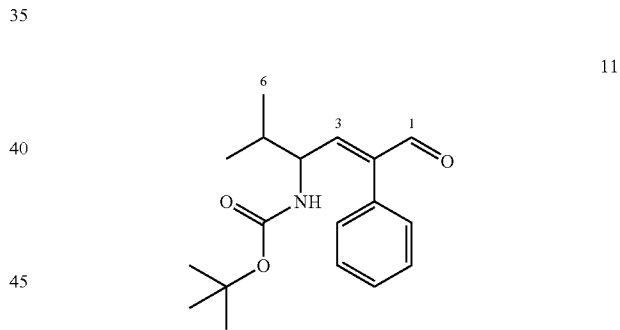

Dess-Martin periodinane (1.44 g, 1.5 eq) is added to a solution of allyl alcohol 10 (690 mg, 2.26 mmol) in CH$_2$Cl$_2$ (30 ml). After 30 minutes of stirring at ambient temperature, ether (50 ml) and a solution saturated with NaHCO$_3$ (30 ml) containing Na$_2$S$_2$O$_3$ (3.0 g) are added. The reaction mixture is stirred until the precipitate is dissolved. After separation of the phases and extraction with ether, the organic phases are washed with brine, dried on MgSO$_4$ and filtered. The residual oil obtained after evaporation of the solvent is purified by passing through an alum tube coated with 3-5 cm of silica (AcOEt/Hept 1/2). The enal 11 (615 mg, 2.03 mmol, clean in 1H NMR) is obtained in the form of a colorless foam.

Yield=90%
Rf=0.56 (AcOEt/Hept 1/1)
$^1$H NMR (300 MHz, CDCl$_3$): δ0.84 (d, 3H. $^3$J=6.8. Hz, H$_6$), 0.87 (d, 3H, $^3$J=6.8 Hz, H$_6'$), 1.43 (s, 9H, (CH$_3$)$_3$), 1.79 (sept, 1H, $^3$J=6.8 Hz, H$_5$), 4.32 (app. q, 1H, $^3$J=8.1 Hz, H$_4$), 4.63 (d, 1H, $^3$J=8.8 Hz, NH), 6.50 (d, 1H, $^3$J=9.1 Hz, H$_3$), 7.26-7.45 (m, 5H, Har), 9.64 (s, 1H, CHO)

¹³C NMR (75 MHz, CDCl₃): δ18.2 (C6), 18.8 (C6'), 28.3 [(CH₃)₃], 32.7 (C5), 54.6 (C4), 79.5 [C(CH₃)₃], 128.1 (CHar), 128.3 (CHar), 129.3 (CHar), 132.1 (^{IV}Car), 144.2 (C2), 153.5 (C3), 155.0 (NCO), 193.7 (CHO)

HRMS (EI): m/z calculated for C₁₈H₂₅NO₃ ([M-C₃H₇']⁺): 260.1287; measured: 260.1277

(2Z)-1-Allyl-2-phenyl-4-[N-tert-butoxycarbonyl)amino]-5-methylhex-2-en-1-ol (12)

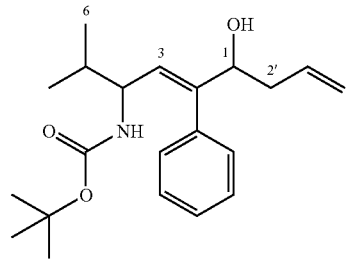

12

The procedure is identical to the preparation of compound 6. The enal 11 (330 mg, 1.09 mmol) leads, after purification on a silica gel (AcOEt/Hept 1/2), to the allyl alcohol 12 (312 mg, 0.90 mmol) in the form of a colorless oil.

Yield=83%
Rf=0.53 (AcOEt/Hept 1/1)
Note: The mixture is composed of 2 diastereoisomer alcohols in a 50/50 proportion according to ¹H NMR.

¹H NMR (300 MHz, CDCl₃): δ0.75 and 0.82 (d, 6H, ³J=7.0 Hz, H₆), 1.37 and 1.41 (s broad, 9H, (CH₃)₃), 1.65 (m, 1H, H₅), 1.83 (s broad, 1H, OH), 2.13 and 2.30 (m, 2H, H₂', 3.82 (m broad, H₄), 4.31 and 4.39 (t(m), 1H, ³J=5.8 Hz, H₁), 4.42 (s broad, 1H, NH), 5.06-5.14 (m, 2H, H₄'), 5.57 and 5.59 (dd, 1H, ³J=9.4, ⁴J=1.1 Hz, H₃), 5.78 (m, 1H, H₃'), 7.19 (t broad, 2H, ³J=4.2 Hz, Har), 7.29-7.37 (m, 3H, Har)

¹³C NMR (75 MHz, CDCl₃): δ18.4, 18.5 (C6 and C6'), 28.4 ([(CH₃)₃]), 33.1 and 33.9 (C5), 40.0 (C2'), 54.1 and 55.3 (C4), 74.2 and 75.1 (C1), 78.8 and 79.3 [C(CH₃)₃], 118.1 and 118.4 (C4'), 127.2 and 127.3 (CHar), 128.2 and 128.3 (CHar), 129.0 and 129.1 (CHar), 134.3 and 134.5 (C3), 137.6 and 137.8 (^{IV}Car), 144.9 and 145.0 (C2), 155.0 (NC=O)

HRMS (EI): m/z calculated for C₁₈H₂₄NO₃ ([M-C₃H₇']⁺): 302.1756; measured: 302.1752

Elemental analysis:
calculated: 73.01% C, 9.04% H, 4.05% N
measured: 72.55% C, 9.27% H, 3.66% N (1-Isopropyl-4-oxo-3-phenyl-hepta-2,6-dienyl)-carbamic acid tert-butyl ester (13)

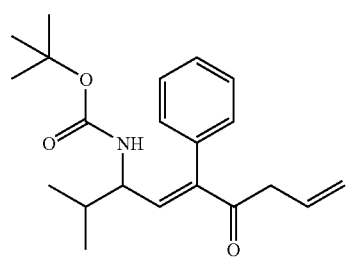

13

Compound 13 is prepared in the same manner as compound 5. It is obtained with an yield of 68.8% after purification by chromatography on a silica gel column (AcOEt/heptane: 1/2 in volume, RF 0.66).

¹H NMR (CDCl₃, 300 MHz): δ0.73 and 0.76 (d, ³J_{HH}=6.90 Hz, 6H, CH₃ iPr), 1.37 (s a, 9H, tBu), 1.64 (hept, ³J_{HH}=6.90 Hz, 1H, CH iPr), 3.22 (d broad, 2H, CO—CH₂—CH=CH₂), 3.92 (m, 1H, N—CH), 4.73 (s broad, 1H, NH), 4.96 (d broad, 1H, CH₂—CH=CH_aH_b), 5.02 (d broad, 1H, CH₂—CH=CH_aH_b), 5.87 (ddt, 1H, CH₂—CH=CH_aH_b), 6.64 (d, ³J_{HH}=9.64 Hz, 1H, NH—CH iPr—CH), 7.10-7.40 (m, 5H, Ph)

¹³C NMR (CDCl₃, 75.47 MHz): δ18.24 and 18.85 (2C, CH₃ iPr), 28.32 (3C, CH₃, tBu), 32.83 (1C, CH iPr), 44.66 (1C, CH₂—CH=CH₂), 54.59 (1C, NH—CH), 78.97 (1C, C^{IV}, tBu), 118.25 (1C, CH=CH₂), 127.76 (1C, p-CH Ph), 128.32 and 129.57 (1C, o-CH and m-CH Ph), 131.12 (1C, CH=C^{IV}), 135.27 (1C, C^{IV} Ph), 141.14 (1C, CH=CH₂), 142.34 (1C, CH=C^{IV}), 154.90 (1C, NH—C=O), 198.82 (1C, CH₂—C=O)

HRMS (EI): m/z C₂₁H₂₉NO₃ ([M-C₄H₈']⁺): theoretical: 287.15214; measured 287.1532 (3 ppm)

2-Allyl-5-isopropyl-3-phenyl-pyrrole-1-carboxylic acid tert-butyl ester (14)

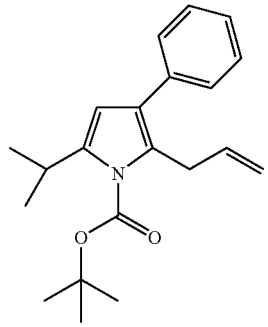

14

Compound 14 is prepared in the same manner as compound 8. It is isolated with a yield of 82.5% after purification by chromatography on a silica gel column (AcOEt/heptane 1/8 in volume, Rf 0.66).

¹H NMR (CDCl₃, 300 MHz): δ1.33 (d, ³J_{HH}=6.8 Hz, 6H, CH₃), 1.67 (s, 9H, tBu), 3.55 (hept, ³J_{HH}=6.8 Hz, 1H, CH iPr), 3.72 (dm, 2H, ³J_{HH}=5.27 Hz, CH₂—CH—CH₂), 4.99 (dm, ³J_{HH}=17.33 Hz (trans), 1H, CH₂—CH=CH_aH_b), 5.13 (dm, ³J_{HH}=10.18 Hz (cis), 1H, CH₂—CH=CCH_bH_a), 6.09 (m, 1H, CH₂—CH=CH₂), 6.17 (s, 1H, CH pyrrole), 7.30 (m, 1H, p-CH, Ph), 7.43 (m, 4H, o-CH+m-CH, Ph).

¹³C NMR (CDCl₃, 75.47 MHz): δ23.21 (2C, CH₃ iPr), 27.01 (1C, CH iPr), 27.93 (3C, CH₃, tBu), 30.61 (1C, CH₂—CH=CH₂), 83.79 (1C, C^{IV}, tBu), 108.29 (1C, CH pyrrole), 115.13 (1C, CH₂—CH=CH₂), 125.39 (1C, C^{IV}), 126.26 (1C, p-CH, Ph), 127.59 (1C, C^{IV}), 128.29 and 128.58 (2C+2C, m-CH+o-CH, Ph), 137.55 (1C, CH₂—CH=CH₂), 136.30 (1C, C^{IV}), 142.30 (1C, C^{IV}), 150.47 (1C, C=O)

2-(3-Hydroxy-propyl)-5-isopropyl-3-phenyl-pyrrole-1-carboxylic acid tert-butyl ester (15)

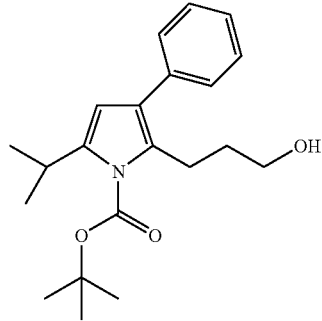

15

Compound 15 is prepared in the same manner as compound 9. It is isolated with a yield of 68.8% after purification by chromatography on a silica gel column (AcOEt/heptane 1/3 in volume, Rf 0.15).

$^1$H NM (CDCl$_3$, 300 MHz): δ1.28 (d, $^3J_{HH}$=6.8 Hz, 6H, CH$_3$), 1.67 (s, 9H, tBu), 1.82 (m, 2H, CH$_2$—CH$_2$—CH$_2$—OH), 3.03 (t, $^3J_{HH}$=7.62 Hz, 2H, CH$_2$—CH$_2$—CH$_2$—OH), 3.47 (sept., $^3J_{HH}$=6.8 Hz, 1H, CH iPr), 3.53 (t, $^3J_{HH}$=6.22 Hz, 2H, CH$_2$—CH$_2$—CH$_2$—OH), 6.07 (s, 1H, CH pyrrole), 7.28 (m, 1H, p-CH, Ph), 7.40 (m, 4H, o-CH+m-CH, Ph)

$^{13}$C NMR (CDCl$_3$, 75.47 MHz): δ22.57 (1C, CH$_2$—CH$_2$—CH$_2$—OH), 23.24 (2C, CH$_3$ iPr), 27.10 (1C, CH iPr), 27.93 (3C, CH$_3$, tBu), 33.47 (1C, CH$_2$—CH$_2$—CH$_2$—OH), 62.09 (1C, CH$_2$—CH$_2$—CH$_2$—OH), 84.05 (1C, C$^{IV}$, tBu), 108.63 (1C, CH pirol), 124.93 (1C, C$^{IV}$), 126.31 (1C, p-CH, Ph), 128.43 and 128.72 (2C+2C, m-CH+o-CH, Ph), 130.37 (1C, C$^{IV}$), 136.39 (1C, C$^{IV}$), 141.94 (1C, C$^{IV}$), 150.70 (1C, C=O)

HRMS (EI): m/z calculated for C$_{21}$H$_{29}$NO$_3$ ([M+']): theoretical: 343.21474; measured: 343.2155 (2 ppm).

1-(tert-Butoxycarbonyl)-2-isopropyl-4-[(2-pyrrolydin-1-ylazo)phenyl]-5-(3-hydroxypropyl)pyrrole (16)

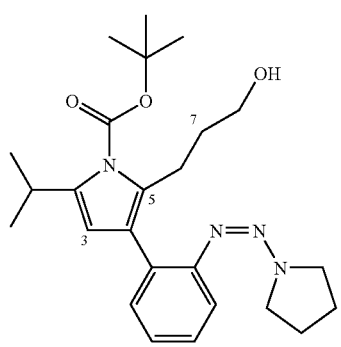

16

Under an argon atmosphere, a mixture of dioxane/water (2.5 ml, 4/1 v/v) containing pyrrole 9 (89 mg, 0.26 mmol), (2-triazenyl)phenylboronic acid (120 mg, 0.51 mmol), potassium carbonate (107 mg, 0.51 mmol) and Pd(Ph$_3$)$_4$ (30 mg, 0.1 eq) is heated at 80° C. overnight. Upon return to ambient temperature, the mixture is evaporated under a vacuum, taken up in ether and chromatographed on a silica gel (AcOEt/Hept 1/3) leading after evaporation of the fractions to the coupling product 16 (44 mg, 0.099 mmol) in the form of a yellow oil.

Yield=39%

Rf=0.17 (AcOEt/Hept 1/3)

$^1$H NMR (300 MHz, CDCl$_3$): δ* 1.20 (d, 6H, $^3$J=6.8 Hz, CH$_3$), 1.64 (s, 9H, (CH$_3$)$_3$), 1.69 (m, 2H, H$_7$), 1.97 (m, 4H, Hh and Hh'), 2.32 (t broad, 1H, $^3$J=6.3 Hz, OH), 2.96 (t, 2H, $^3$J=6.5 Hz, H$_6$), 3.32 (m, 2H, H$_8$), 3.46 (app quint, 1H, $^3$J=6.8 Hz, CH(CH$_3$)), 3.50-3.90 (large, 4H, Hg and Hg'), 5.93 (d, 1H, $^4$J=0.9 Hz, H$_3$), 7.15 (td, 1H, $^3$J=7.9 Hz, $^4$J=1.5 Hz, He or Hd), 7.23-7.29 (m, 2H, Hf and Hd or He), 7.40 (d, 1H, $^3$J=7.9 Hz, Hc)

$^{13}$C NMR (75 MHz, CDCl$_3$): δ* 23.4 (CH$_3$), 23.8 (Ch and Ch'), 24.1 (C6), 27.1 [CH(CH$_3$)$_2$], 28.0 [(CH$_3$)$_3$], 32.6 (C7), 47.6 (broad signal Cg and Cg'), 61.9 (C8), 83.4 [C(CH$_3$)$_3$], 111.2 (C3), 117.5 (Cc), 123.6, 130.7, 130.8 (Ca, C4 and C5), 125.1, 127.7, 131.3 (Ce, Cd and Cf), 141.2 (C2), 149.6 (Cb or NC=O), 150.8 (NC=O or Cb)

* The attributions are confirmed by $^3$H⇌$^{13}$C correlation.

HRMS (FAB+): m/z calculated for C$_{25}$H$_{37}$N$_4$O$_3$ ([M+H]$^+$): 441.2866; measured: 441.2863

3-(2-Amino-phenyl)-2-(3-hydroxy-propyl)-5-isopropyl-pyrrole-1-carboxylic acid tert-butyl ester (17)

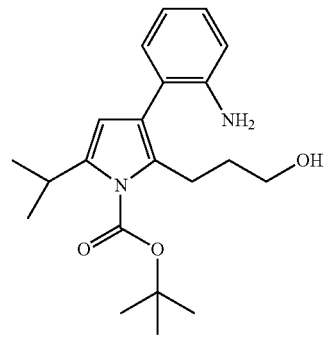

17

In an autoclave reactor, compound 16 (0.340 g, 0.772 mmol) is placed in the presence of an equivalent mass of Raney nickel (washed successively beforehand with water degassed to neutral pH, with absolute ethanol then with methanol) in a methanol/ethyl acetate mixture. The mixture is maintained at 25° C. under 20 bar of dihydrogen overnight. The suspension is then filtered on celite. The celite is rinsed with ether. The filtrate obtained is then evaporated. The residue obtained is purified by chromatography on a silica gel column (AcOEt/heptane 1/2 in volume, Rf 0.1). Compound 17 is isolated with a yield of 80.2% (0.222 g) in the form of a slightly red oil.

$^1$H NMR (CDCl$_3$, 300 MHz): δ1.22 (d, $^3J_{HH}$=5.49 Hz, 6H, CH$_3$ iPr), 1.65 (s, 9H, CH$_3$ tBu), 1.68 (m, 2H, CH$_2$—CH$_2$—CH$_2$—OH), 2.83 (t, $^3J_{HH}$=7.11 Hz, 2H, CH$_2$—CH$_2$—CH$_2$—OH), 3.43 (t, $^3J_{HH}$=6.11 Hz, 2H, CH$_2$—CH$_2$—CH$_2$—OH), 3.48 (m, 1H, CH iPr), 5.96 (s, 1H, CH pyrrole), 6.73-6.80 (m, 2H, CH arom.), 7.05-7.13 (m, 2H, CH arom.)

$^{13}$C NMR (CDCl$_3$, 75.47 MHz): δ22.60 (1C, CH$_2$—CH$_2$—CH$_2$—OH), 23.22 (1C, CH$_3$ iPr), 27.12 (1C, CH iPr), 27.92 (3C, CH$_3$, tBu), 32.88 (1C, CH$_2$—CH$_2$—CH$_2$—OH), 61.47 (1C, CH$_2$—CH$_2$—CH$_2$—OH), 84.05 (1C, $C^{IV}$ tBu), 108.43 (1C, CH arom. pyrrole), 115.23 (1C, CH arom.), 118.46 (1C, $\underline{CH}$ arom.), 121.31 (1C, $C^{IV}$ arom. pyrrole), 121.80 (1C, $C^{IV}$ arom. Ph), 128.29 (1C, $\underline{C}H$ arom.), 131.09 (1C, CH arom.), 131.45 (1C, $CH_2$-$C^{IV}$ arom. pyrrole), 142.50 (1C, iPr—$C^{IV}$ arom. pyrrole), 144.49 (1C, N—$C^{IV}$ arom. Ph), 150.61 (1C, $\underline{C}O$ Boc)

HRMS (EI): m/z calculated for $C_{21}H_{30}N_2O_3$ ([M$^+$]): theoretical: 358.22564; measured: 358.2218 (10 ppm)

3-(5-Isopropyl-3-phenyl-1H-pyrrol-2-yl)-propan-1-ol (18)

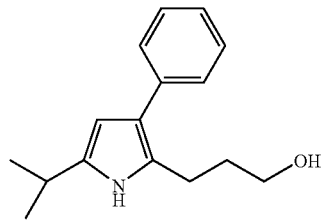

18

In a 100 ml flask containing compound 15 (0.197 g, 0.57 mmol), 3.7 ml (8.7 mmol) of a 2.33 M solution of anhydrous sodium methanolate in methanol are added. The solution is left stirring at ambient temperature for 72 h. The solvent is then evaporated with a rotary evaporator. 5 ml of an aqueous solution saturated with ammonium chloride are added to the residue obtained. The solution thus obtained is extracted with ether. After separation of the phases, the organic phase is washed with brine then dried on $MgSO_4$. After separation of the magnesium salts by filtration, the ether is evaporated. The residue obtained is purified by chromatography on a silica gel column (AcOEt/heptane 1/2 in volume, Rf 0.1). Compound 18 is isolated with a yield of 86.4% (0.121 g) in the form of a brown oil.

$^1$H NMR (CDCl$_3$, 300 MHz): δ1.33 (d, $^3J_{HH}$=6.86 Hz, 6H, C$\underline{H}_3$ iPr), 1.91 (m, 2H, CH$_2$—C$\underline{H}_2$—CH$_2$—OH), 2.14 (s a, 1H, O$\underline{H}$), 2.91 (t, $^3J_{HH}$=7.3 Hz, 2H, C$\underline{H}_2$—CH$_2$—CH$_2$—OH), 2.95 (sept., $^3J_{HH}$=6.86 Hz, 1H, C$\underline{H}$ iPr), 3.71 (t, $^3J_{HH}$=6.0 Hz, 2H, CH$_2$—CH$_2$—C$\underline{H}_2$—OH), 6.06 (m, 1H, C$\underline{H}$ pyrrole), 7.22 (m, 1H, p-C$\underline{H}$ Ph), 7.42 (m, 4H, o-C$\underline{H}$+m-C$\underline{H}$, Ph), 8.38 (s, 1H, N$\underline{H}$)

$^{13}$C NMR (CDCl$_3$, 75.47 MHz): δ 22.61 (2C, $\underline{C}H_3$ iPr), 22.99 (1C, $\underline{C}H_2$—CH$_2$—CH$_2$—OH), 27.01 (1C, $\underline{C}H$ iPr), 32.43 (1C, CH$_2$—$\underline{C}H_2$—CH$_2$—OH), 62.25 (1C, CH$_2$—CH$_2$—$\underline{C}H_2$—OH), 103.50 (1C, CH pirol), 120.67 (1C, $C^{IV}$), 125.04 (1C, p-CH, Ph), 126.13 (1C, $C^{IV}$), 127.72 and 128.36 (2C+2C, m-$\underline{C}H$+o-CH, Ph), 137.46 (1C, $C^{IV}$), 137.48 (1C, $C^{IV}$)

HRMS (EI): m/z calculated for $C_{16}H_{21}NO$ ([M$^+$]): theoretical: 243.16231; measured: 243.1607 (6 ppm)

3-[3-(2-Amino-phenyl)-5-isopropyl-1H-pyrrol-2-yl]-propan-1-ol (19)

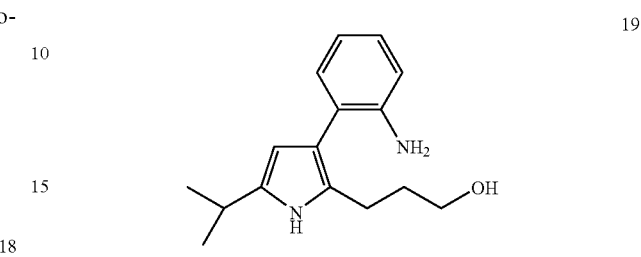

19

Compound 19 is prepared from compound 17 in the same way as compound 18. It is obtained with a yield of 51.7% after purification by chromatography on a silica gel column (AcOEt/heptane 1/1 in volume, Rf 0.21).

$^1$H NMR (CDCl$_3$, 300 MHz): δ1.29 (d, $^3J_{HH}$=6.85 Hz, 6H, C$\underline{H}_3$ iPr), 1.77 (m, 2H, CH$_2$—C$\underline{H}_2$—CH$_2$—OH), 2.66 (t, $^3J_{HH}$=7.08 Hz, 2H, C$\underline{H}_2$—CH$_2$—CH$_2$—OH), 2.92 (hept, $^3J_{HH}$=6.87 Hz, 1H, CH i$\underline{P}r$), 3.59 (t, $^3J_{HH}$=5.93 Hz, 2H, CH$_2$—CH$_2$—C$\underline{H}_2$—OH), 5.89 (m, 1H, CH pyrrole), 6.76-6.82 (m, 2H, C$\underline{H}$ arom.), 7.08-7.28 (m, 2H, C$\underline{H}$ arom.), 8.27 (s, 1H, NH pyrrole)

$^{13}$C NMR (CDCl$_3$, 75.47 MHz): δ22.36 (1C, $\underline{C}H_2$—CH$_2$—CH$_2$—OH), 22.59 (2C, $\underline{C}H_3$ iPr), 27.04 (1C, $\underline{C}H$ iPr), 32.24 (1C, $CH_2\underline{C}H_2$—CH$_2$—OH), 61.69 (1C, $\underline{C}H_2$—CH$_2$—CH$_2$—OH), 108.96 (1C, CH arom. pyrrole), 115.19 (1C, $\underline{C}H$ arom.), 117.08 (1C, $C^{IV}$—$C^{IV}$ pyrrole), 118.44 (1C, $\underline{C}H$ arom. pyrrole), 123.48 (1C, $C^{IV}$ arom. Ph), 127.03 (1C, $\underline{C}H_2$—$C^{IV}$ arom.), 127.40 (1C, CH arom.), 131.21 (1C, CH arom. pyrrole), 137.64 (1C, iPr—$C^{IV}$ arom. pyrrole), 144.51 (1C, N$C^{IV}$ arom. Ph)

HRMS (EI): m/z calculated for $C_{16}H_{22}N_2O$ ([M$^+$]): theoretical: 258.17321; measured: 258.1727 (1 ppm)

2-(3-Hydroxy-propyl)-5-isopropyl-pyrrole-1-carboxylic acid tert-butyl ester (20)

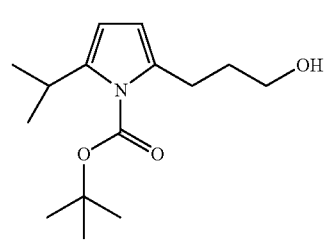

20

Compound 20 is a sub-product obtained in low quantity during the synthesis of compound 16 from compound 9. It is isolated from the reaction mixture after the hydrogenation step enabling the passage of compound 16 into compound 17 by purification by chromatography on a silica gel column (AcOEt/heptane 1/3 in volume, Rf 0.17).

$^1$H NMR (CDCl$_3$, 300 MHz): δ1.21 (d, $^3J_{HH}$=6.74 Hz, 6H, C$\underline{H}_3$ iPr), 1.62 (s, 9H, C$\underline{H}_3$ tBu), 1.89 (m, 2H+1H, CH$_2$—C$\underline{H}_2$—CH$_2$—OH), 2.87 (t, $^3J_{HH}$=7.45 Hz, 2H, C$\underline{H}_2$), 3.42

(hept, $^3J_{HH}$=6.78 Hz, 1H, C$\underline{H}$iPr), 3.69 (t, $^3J_{HH}$=6.31 Hz, 2H, C$\underline{H}_2$), 5.89 (m, 2H, CH pyrrole).

$^{13}$C NMR (CDCl$_3$, 75.47 MHz): δ23.25 (2C, $\underline{C}$H$_3$ iPr), 25.66 (1C, CH$_2$—$\underline{C}$H$_2$—CH$_2$—OH), 27.18 (1C, $\underline{C}$H iPr), 27.95 (3C, $\underline{C}$H$_3$ tBu), 32.31 (1C, $\underline{C}$H$_2$—CH$_2$—CH$_2$—OH), 62.34 (1C, $\underline{C}$H$_2$—CH$_2$—CH$_2$—O$\underline{H}$), 83.70 (1C, $\underline{C}^{IV}$ tBu), 106.55 (1C, CH pyrrole), 109.20 (1C, CH pyrrole), 135.17 (1C, CH$_2$—$\underline{C}^{IV}$ pyrrole), 142.61 (1C, iPr—$\underline{C}^{IV}$ pyrrole), 150.61 (1C, $\underline{C}$O Boc)

3-(5-Isopropyl-1H-pyrrol-2-yl)-propan-1-ol (21)

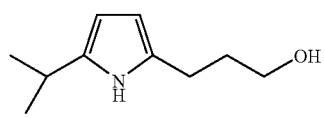

Compound 21 is prepared from compound 20 in the same way as compound 18. Compound 21 is isolated with a yield of 97.8% after purification by chromatography on a silica gel column (AcOEt/heptane 1/1 in volume, Rf 0.37).

$^1$H NMR (CDCl$_3$, 300 MHz): δ1.29 (d, $^3J_{HH}$=6.86 Hz, 6H, CH$_3$ iPr), 1.90 (m, 2H, CH$_2$—C$\underline{H}_2$—CH$_2$—OH), 2.07 (s, 1H, O$\underline{H}$), 2.71 (t, $^3J_{HH}$=7.35 Hz, 2H, C$\underline{H}_2$—CH$_2$—CH$_2$—OH), 2.91 (hept, $^3J_{HH}$=6.87 Hz, 1H, CH iPr), 3.73 (t, $^3J_{HH}$=6.12 Hz, 2H, CH$_2$—CH$_2$—C$\underline{H}_2$—OH), 5.83 (m, 2H, CH pyrrole), 8.10 (s, 1H, NH).

$^{13}$C NMR (CDCl$_3$, 75.47 MHz): δ23.69 (2C, CH$_3$ iPr), 24.29 (1C, CH$_2$—$\underline{C}$H$_2$—CH$_2$—OH), 27.06 (1C, $\underline{C}$H iPr), 32.34 (1C, $\underline{C}$H$_2$—CH$_2$—CH$_2$—OH), 62.40 (1C, CH$_2$—CH$_2$—$\underline{C}$H$_2$—OH), 102.60 (1C, CH pyrrole), 104.54 (1C, CH pyrrole), 130.21 (1C, CH$_2$-$\underline{C}^{IV}$ pyrrole), 137.86 (1C, iPr—$\underline{C}^{IV}$ pyrrole)

HRMS (EI): m/z calculated for C$_{10}$H$_{17}$NO ([M$^{+\bullet}$]): theoretical: 167.13101; measured: 167.1320 (5 ppm).

II. BIOLOGICAL ANALYSES

Aim: Given the role of tubulin in the formation of the mitotic spindle, we analyzed the effect of the compounds according to the present invention on the cell cycle of the following murine cells using various methods: the murine melanoma tumor cell line, the B16 F1 cell line and the mel a cell line (melanocytes), and the L1210 mouse leukemia cell line.

1) The Effect of Compounds 17, 18, 19 and 21 on Cell Growth.

We initially evaluated the effect of compounds 17, 18 and 19 on the growth of the three cell lines by a "MTT" test. The principle of the MTT test consists of measuring the activity of mitochondrial succinate dehydrogenase in living cells. This enzyme transforms MTT (3-(4,5-dimethylthiazol-2-yl)-2,5-diphenyltetrazolium bromide), yellow in color, into insoluble purple formazan crystals. After dissolution of the crystals in dimethylsulfoxide (DMSO), absorbance is measured at 540 nm by spectrophotometry. The optical densities obtained are directly proportional to the number of living cells. The cytotoxic effect of a sample is evaluated by the percentage of living cells in the presence of this sample, compared to the cells treated with the solvent alone. This method makes it possible to measure the proportion of living cells in a given cell population. By comparison with untreated cells, we thus determined the concentration of each compound that induces a 50% inhibition of cell growth. The results obtained are presented in table 1. The IC$_{50}$ ranges from 50 µM to 100 µM.

TABLE 1

Comparison of the effect of compounds on the growth of B16 F1 cells, mel a melanocytes and L1210 mouse leukemias.

| Compounds | | IC$_{50}$* (µM) ± sd | |
|---|---|---|---|
| | B16 F1 | Mel a | L1210 |
| 17 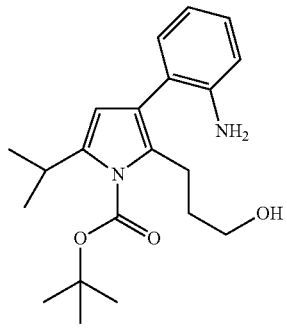 | 88.7 ± 7.6 | 69.7 ± 0.9 | 53.7 ± 0.7 |
| 19 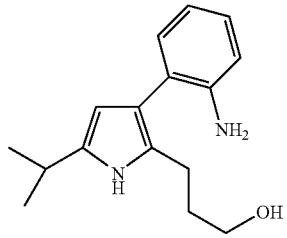 | 106.7 ± 1.8 | 116.1 ± 3.2 | 17.7 ± 4.5 |

TABLE 1-continued

Comparison of the effect of compounds on the growth of
B16 F1 cells, mel a melanocytes and L1210 mouse leukemias.

| Compounds | | $IC_{50}$* (µM) ± sd | |
|---|---|---|---|
| | B16 F1 | Mel a | L1210 |
| 18 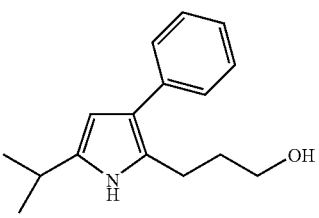 | 171.0 ± 10.8 | n.d. | 33.2 ± 1.3 |
| 21 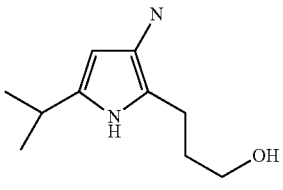 | >400 | n.d. | >400 |

*The $IC_{50}$ is the concentration that inhibits 50% of cell growth. The values given represent the mean ± standard deviation of 3 different experiments carried out in triplicate.

The antiproliferative character of the compounds varies according to the cell line studied and to the compound analyzed. A better $IC_{50}$ is observed in the presence of compound 19 on the L1210 (mouse leukemia) cells.

Compound 21 is not functionalized at position 3 of the pyrrole nucleus. It serves as a reference and demonstrates that position 3 of the pyrrole nucleus is a strategic position for obtaining biological activity.

2) The Effect of the Compounds on the Progression of the Cell Cycle

In order to approach the mechanism of action of these compounds, we then studied their effect on the progression of the cell cycle in mouse melanoma (B16) cells and mouse leukemia (L1210) cells. For this purpose, we compared the distribution of the treated or untreated cells in each phase of the cycle. The cells were treated for 24 hours at concentrations near the $IC_{50}$ of each compound. They then were fixed and made permeable with ethanol. After incubation with propidium iodide, which labels cellular DNA, the DNA content of the cells is then analyzed by flow cytometry. The results obtained are presented in table 2.

TABLE 2

Effect of the compounds on the progression of the
cell cycle. Analysis by flow cytometry after labeling with
propidium iodide.

| | % of B16 cells[a] | | | % of L1210 cells | | |
|---|---|---|---|---|---|---|
| | In phase G1 | In phase S | In phase G2/M | In phase G1 | In phase S | In phase G2/M |
| Control | 47.8 ± 6.2 | 43.7 ± 2.9 | 8.5 ± 4.3 | 29.4 | 60.7 | 10.0 |
| Compound 17 | | | | | | |
| 40 µM | — | — | — | 54.9 | 21.9 | 23.2 |
| 50 µM | 58.0 | 16.6 | 25.4 | 39.2 | 17.2 | 43.6 |
| 70 µM | 40.8 | 37 | 22.3 | — | — | — |
| 100 µM | 43.3 | 40.3 | 16.5 | — | — | — |

TABLE 2-continued

Effect of the compounds on the progression of the
cell cycle. Analysis by flow cytometry after labeling with
propidium iodide.

| | % of B16 cells[a] | | | % of L1210 cells | | |
|---|---|---|---|---|---|---|
| | In phase G1 | In phase S | In phase G2/M | In phase G1 | In phase S | In phase G2/M |
| Compound 19 | | | | | | |
| 50 µM | 78.7 | 14.1 | 5.2 | 49.5 | 26.5 | 24 |
| 75 µM | 56.1 | 2.8 | 31.9 | 39.8 | 21.4 | 38.8 |
| Compound 18 | | | | | | |
| 40 µM | — | — | — | 32.7 | 54.7 | 12.6 |
| 55 µM | — | — | — | 30.9 | 47.2 | 21.9 |
| 75 µM | 65.0 | 11.3 | 12.1 | — | — | — |
| 125 µM | 50.0 | 5.2 | 32.0 | — | — | — |
| 150 µM | 42.1 | 21.8 | 36.0 | — | — | — |

[a]For compounds 19 and 18, except at 150 µM, the values indicated represent the mean ± sd of at least 2 experiments. For compound 17, the value indicated is that of a single experiment.

For concentrations below the $IC_{50}$, we observe an accumulation of cells in phase G1 (gap 1), as well as a reduction in the quantity of cells in phase S (DNA synthesis). The cells treated with concentrations near $IC_{50}$, or with higher concentrations, exhibited a higher proportion of cells in phase G2/M (gap 2/mitosis) (approximately 3 times more for compound 2). In contrast, the proportion of cells in phase G1 seem to be "normalized," that is to say, the proportion of cells in G1 is not changed. For the highest concentrations, the quantity of cells in phase S also appears to approach the values of the control cells.

The method of labeling with propidium iodide does not make it possible to distinguish the cells which replicate their DNA actively. Thus we cannot affirm that the cells observed in phase S in the treated cells (that is to say, having a 4n quantity of DNA) are actually the cells which replicate their DNA actively or if they are simply locked in phase S.

To try to elucidate this problem, we incubated treated or untreated cells with bromodeoxyuridine (BrdU) for a short period of time (pulse). BrdU incorporates into replicating cellular DNA. After fixing, the cells are made permeable then incubated in the presence of an anti-BrdU antibody labeled with a fluorochrome. The cells are also labeled with propidium iodide, then analyzed by flow cytometry.

The profiles obtained (table 2) demonstrate that the cells treated with concentrations greater than or equal to the $IC_{50}$ do not incorporate BrdU at all. Thus, these cells are no longer replicating their DNA.

The invention claimed is:

1. A compound represented by following formula I:

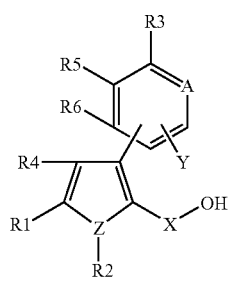

in which:
Z represents N, O or S,
R1, R3, R4, R5 and R6 represent independently of one another an atom of hydrogen, an atom of fluorine, a $C_1$-$C_{12}$ linear or branched alkyl group, a $C_3$-$C_{12}$ cycloalkyl group, a $C_2$-$C_{12}$ linear or branched alkenyl group, a $CH_2$—B or $CH_2$—$CH_2$—B group in which B represents
  a phenyl group possibly substituted by one or more groups chosen among a $C_1$-$C_6$ linear or branched alkyl group, a $C_1$-$C_6$ linear or branched alkoxy group, a $NH_2$ group, a $NO_2$ group, a CN group, a COOH group, a $C_1$-$C_6$ linear or branched $CO_2$(alkyl) group, a $CONH_2$ group, a $C_1$-$C_6$ linear or branched CONH(alkyl) group, a $C_1$-$C_6$ linear or branched CON(alkyl)$_2$ group, a Cl atom, a Br atom, an I atom, an OH group, a $COCF_3$ group, an $OSO_2CF_3$ group;
  a naphthyl group;
  an anthracenyl group;
  a 9H-fluorenyl group possibly substituted at position 9 by one or two $C_1$-$C_{12}$ linear or branched alkyl groups;
  an anisyl group or a pyridinyl group;
R2 represents H, a $C_1$-$C_{12}$ linear or branched alkyl group, a phenyl group, a benzyl group, a $C_1$-$C_6$ linear or branched $CO_2$(alkyl) group, a $CO_2$(benzyl) group, a $C_3$-$C_6$ linear or branched $CO_2$(alkenyl) group, a tosyl group, a mesyl group, a 9-fluorenylmethoxycarbonyl (FMOC) group, a $NH_2$ group or a $C_1$-$C_6$ linear or branched NH(alkyl) group, a $C_1$-$C_6$ linear or branched N(alkyl)$_2$ group, NH tertiobutyloxycarbonyl, $NHCO_2CH_2$ phenyl or R2 is absent when Z represents O or S;
X represents a $C_1$-$C_{12}$ linear or branched alkyl group, a $C_1$-$C_{12}$ linear or branched hydroxyalkyl group or a $C_1$-$C_{12}$ linear or branched aminoalkyl group;
A represents a CH group, a nitrogen atom or a $NL^+$ group in which L represents a $C_1$-$C_{12}$ linear or branched alkyl group;
Y represents an atom of hydrogen, a $C_1$-$C_{12}$ linear or branched alkyl group, a $C_3$-$C_{12}$ cycloalkyl group, an OH group, a CN group, a $N_3$ group, a $C_1$-$C_{12}$ linear or branched alkoxy group, a $C_1$-$C_{12}$ linear or branched hydroxyalkyl group, a $C_1$-$C_{12}$ linear or branched aminoalkyl group, $N_2^+$, a NZ1-NHZ2, NH—NZ1Z2 or NZ1Z2 group in which Z1 and Z2 represent independently of one another an atom of hydrogen, a $C_1$-$C_{12}$ linear or branched alkyl group, a $C_3$-$C_{12}$ cycloalkyl group, a phenyl group possibly substituted by one or more groups chosen among a $C_1$-$C_6$ linear or branched alkyl group, a $C_1$-$C_6$ linear or branched alkoxy group, a $NH_2$ group, a CN group, a COOH group, a $C_1$-$C_6$ linear or branched $CO_2$(alkyl) group, a $CONH_2$ group, a $C_1$-$C_6$ linear or branched CONH(alkyl) group, a $C_1$-$C_6$ linear or branched CON(alkyl)$_2$ group, a Cl atom, a Br atom, an I atom, an OH group, a $COCF_3$ group, an $OSO_2CF_3$ group, a benzyl group, an anisyl group, a pyridinyl group, C(O)—W, C(S)—W or C(NH)—W in which
  W represents a $C_1$-$C_{12}$ linear or branched alkyl group, a $C_3$-$C_{12}$ cycloalkyl group, a $C_1$-$C_{12}$ linear or branched alkoxy group, a $C_1$-$C_{12}$ linear or branched alkylthio group or NQQ1 in which
    Q and Q1 represent independently of one another an atom of hydrogen, a $C_1$-$C_{12}$ linear or branched alkyl group, a $C_3$-$C_{12}$ cycloalkyl group or CH(M) $CO_2M1$ in which
      M and M1 represent independently of one another a hydrogen atom, a $C_1$-$C_{12}$ linear or branched alkyl group, a $C_3$-$C_{12}$ cycloalkyl group, a $C_2$-$C_{12}$ linear or branched alkenyl group, a phenyl group, a benzyl group, a $CH_2$—B or $CH_2$—$CH_2$—B group in which B is as defined above, with the exception of the following formulas:

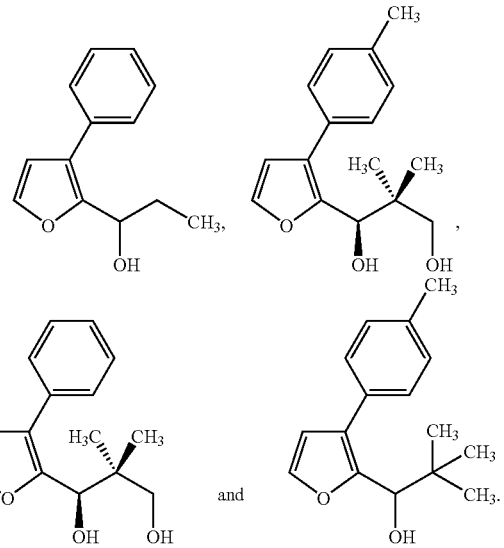

2. A compound according to claim 1 in which Z represents N.

3. A compound according to claim 1 in which A represents the group CH.

4. A compound according to claim 1 in which Y represents a $NH_2$ group or an atom of hydrogen.

5. A compound according to claim 1 in which X represents a $C_1$-$C_{12}$ linear or branched alkyl group.

6. A compound according to claim 1 wherein said compound is selected from the group consisting of:

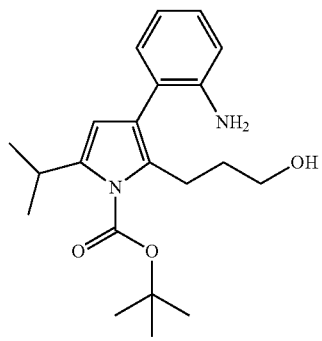

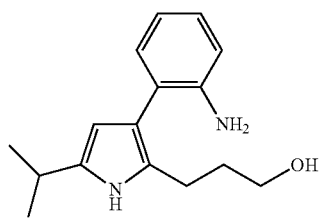

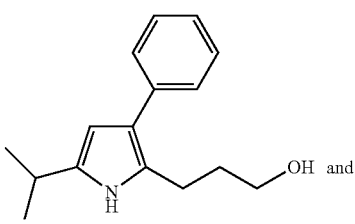

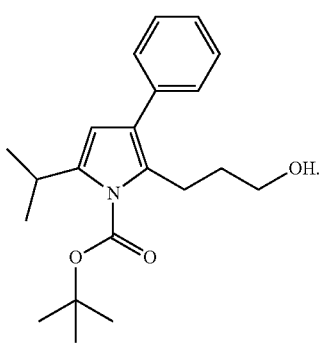

7. A method of preparing compounds according to claim 1 comprising the steps of:
  a) synthesizing a pyrrolylalkylcarbinole, furanylalkylcarbinole or thiophenylalkylcarbinole unit of following formula II:

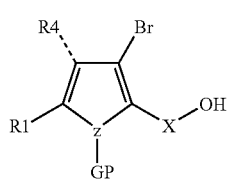

in which Z, X, R1 and R4 are as defined in claim 1 and GP represents a nitrogen protective group when Z represents N, or is absent when Z represents O or S, and
  b) functionalizing the pyrrolylalkylcarbinole, furanylalkylcarbinole, or thiophenylalkylcarbinole unit by introducing an aryl or heteroaryl unit at position 3 of the pyrrole, furan or thiophene ring.

8. A method according to claim 7 wherein X represents $(CH_2)_3$, and wherein step a) consists of the cyclodehydration of unsaturated β-γ aminoketones of following formula III:

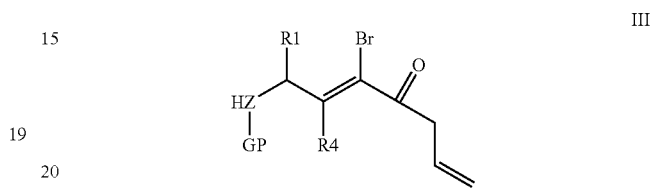

in which Z, R1, R4 and GP are as defined in claim 7 in order to obtain the product of following formula IV:

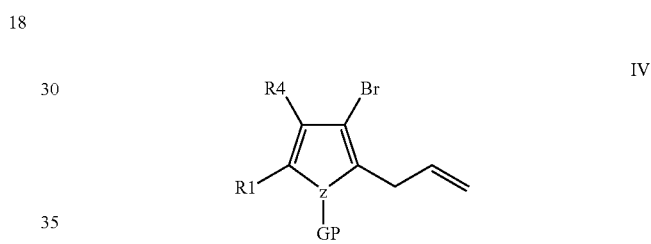

in which Z, R1, R4 and GP are as defined in claim 7,
followed by the introduction of the alcohol function by hydroboration-oxidation of the product of formula IV in order to obtain the product of formula II as defined in claim 7.

9. A method according to claim 7 wherein R2, R3, R4, R5 and R6 represent an atom of hydrogen, Y represents a $NH_2$ group, A represents a CH group, X represents $(CH_2)_3$ and Z represents N, wherein step b) consists of:
  a palladium-catalyzed Suzuki-Miyaura cross-coupling of the compound of formula II, in which R4 represents an atom of hydrogen, X represents $(CH_2)_3$, Z represents N and GP represents a nitrogen protective group, and of 2-triazene boronic acid in order to obtain a compound of following formula V:

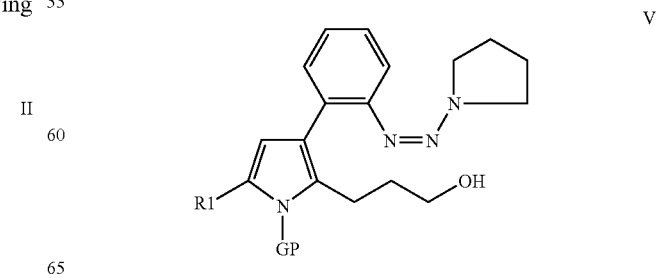

in which GP represents a nitrogen protective group, deprotection of the triazene function in order to obtain the group of following formula VI:

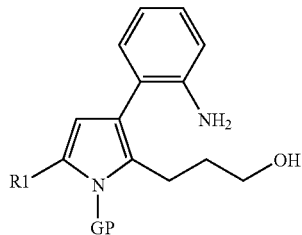

VI in which GP represents a nitrogen protective group, specific deprotection of protective group GP in order to obtain the compound of formula I in which R2, R3, R4, R5 and R6 represent an atom of hydrogen, Y represents a $NH_2$ group, A represents a CH group, X represents $(CH_2)_3$, and Z represents N.

10. A pharmaceutical composition comprising a compound according to claim 1 or a compound selected from the group consisting of:

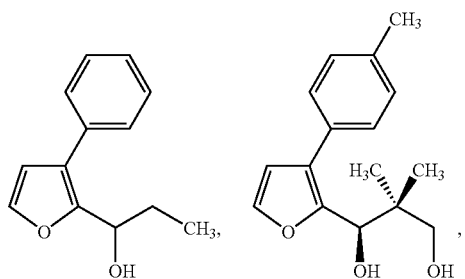

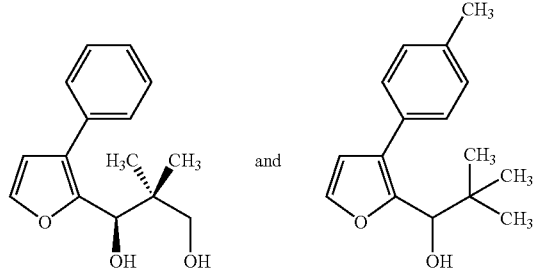

and a pharmaceutically acceptable excipient.

11. A compound of formula V:

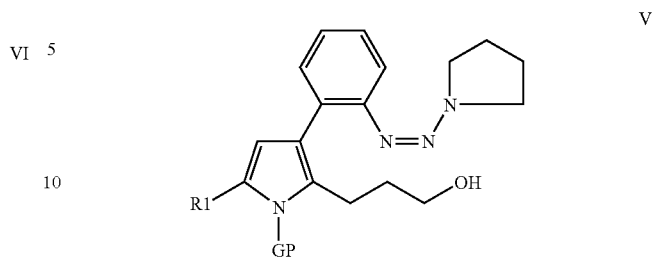

V in which GP represents a nitrogen protective group and R1 represents an atom of hydrogen, an atom of fluorine, a $C_1$-$C_{12}$ linear or branched alkyl group, a $C_3$-$C_{12}$ cycloalkyl group, a $C_2$-$C_{12}$ linear or branched alkenyl group, a $CH_2$—B or $CH_2$—$CH_2$—B group in which B represents a phenyl group possibly substituted by one or more groups chosen among a $C_1$-$C_6$ linear or branched alkyl group, a $C_1$-$C_6$ linear or branched alkoxy group, a $NH_2$ group, a $NO_2$ group, a CN group, a COOH group, a $C_1$-$C_6$ linear or branched $CO_2$(alkyl) group, a $CONH_2$ group, a $C_1$-$C_6$ linear or branched CONH(alkyl) group, a $C_1$-$C_6$ linear or branched CON(alkyl)$_2$ group, a Cl atom, a Br atom, an I atom, an OH group, a $COCF_3$ group, an $OSO_2CF_3$ group; a naphthyl group; an anthracenyl group; a 9H-fluorenyl group possibly substituted at position 9 by one or two $C_1$-$C_{12}$ linear or branched alkyl groups; an anisyl group or a pyridinyl group.

12. A compound of formula VI:

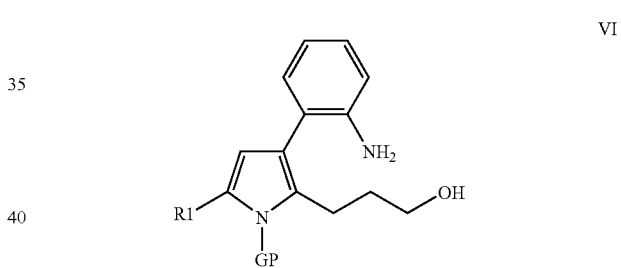

VI in which GP represents a nitrogen protective group and R1 represents an atom of hydrogen, an atom of fluorine, a $C_1$-$C_{12}$ linear or branched alkyl group, a $C_3$-$C_{12}$ cycloalkyl group, a $C_2$-$C_{12}$ linear or branched alkenyl group, a $CH_2$—B or $CH_2$—$CH_2$—B group in which B represents a phenyl group possibly substituted by one or more groups chosen among a $C_1$-$C_6$ linear or branched alkyl group, a $C_1$-$C_6$ linear or branched alkoxy group, a $NH_2$ group, a $NO_2$ group, a CN group, a COOH group, a $C_1$-$C_6$ linear or branched $CO_2$(alkyl) group, a $CONH_2$ group, a $C_1$-$C_6$ linear or branched CONH(alkyl) group, a $C_1$-$C_6$ linear or branched CON(alkyl)$_2$ group, a Cl atom, a Br atom, an I atom, an OH group, a $COCF_3$ group, an $OSO_2CF_3$ group; a naphthyl group; an anthracenyl group; a 9H-fluorenyl group possibly substituted at position 9 by one or two $C_1$-$C_{12}$ linear or branched alkyl groups; an anisyl group or a pyridinyl group.

* * * * *